US010770183B2

(12) United States Patent
Huentelman et al.

(10) Patent No.: US 10,770,183 B2
(45) Date of Patent: Sep. 8, 2020

(54) METHODS OF ASSESSING A RISK OF DEVELOPING NECROTIZING MENINGOENCEPHALITIS

(71) Applicants: The Translational Genomics Research Institute, Phoenix, AZ (US); University of Georgia Research Foundation, Inc., Athens, GA (US)

(72) Inventors: Matthew Huentelman, Phoenix, AZ (US); Scott Schatzberg, Algodones, NM (US); Renee Barber, Athens, GA (US)

(73) Assignees: The Translational Genomics Research Institute, Phoenix, AZ (US); University of Georgia Research Foundation, Inc., Athens, GA (US)

(*) Notice: Subject to any disclaimer, the term of this patent is extended or adjusted under 35 U.S.C. 154(b) by 24 days.

(21) Appl. No.: 16/167,463

(22) Filed: Oct. 22, 2018

(65) Prior Publication Data

US 2019/0051418 A1 Feb. 14, 2019

Related U.S. Application Data

(63) Continuation of application No. 14/713,134, filed on May 15, 2015, now Pat. No. 10,147,505, which is a continuation-in-part of application No. 13/905,109, filed on May 29, 2013, now abandoned, and a continuation-in-part of application No. 13/698,907, filed as application No. PCT/US2011/037262 on May 19, 2011, now abandoned.

(60) Provisional application No. 61/993,399, filed on May 15, 2014, provisional application No. 61/652,732, filed on May 29, 2012, provisional application No. 61/346,309, filed on May 19, 2010.

(51) Int. Cl.
| | |
|---|---|
| C07H 21/04 | (2006.01) |
| C12Q 1/68 | (2018.01) |
| G16H 50/30 | (2018.01) |
| C12Q 1/6883 | (2018.01) |
| A01K 67/02 | (2006.01) |

(52) U.S. Cl.
CPC ........... *G16H 50/30* (2018.01); *C12Q 1/6883* (2013.01); *A01K 67/02* (2013.01); *C12Q 2600/106* (2013.01); *C12Q 2600/118* (2013.01); *C12Q 2600/124* (2013.01); *C12Q 2600/156* (2013.01); *C12Q 2600/172* (2013.01)

(58) Field of Classification Search
CPC .................. C12Q 1/6883; C12Q 2600/156
USPC .......................................................... 506/2
See application file for complete search history.

(56) References Cited

U.S. PATENT DOCUMENTS

| 5,474,796 A | 12/1995 | Brennan | |
|---|---|---|---|
| 2013/0157873 A1* | 6/2013 | Huentelman | ........ C12Q 1/6883 506/2 |

OTHER PUBLICATIONS

Safra et al. (Veterinary Journal, vol. 189, pp. 220-226, 2011) (Year: 2011).*
Greer et al. (Tissue Antigens, vol. 76, pp. 110-118, 2010) (Year: 2010).*
Pedersen et al. (J. Vet Diag. Invest. vol. 23, pp. 68-76, Edat, Jan. 11, 2011) (Year: 2011).*
Barber et al. (The Am. Genetic Association, J. of Heredity, vol. 102, S1, pp. S40-S46, EDAT: Aug. 24, 2011 (Year: 2011).*
Illumina CanineHD BeadChip Data Sheet, Nov. 2009, pp. 1-4.
Pedersen et al., "Dog leukocyte antigen class II-associated genetic risk testing for immune disorders of dogs: simplified approaches using pug dog necrotizing meningoencephalitis as a model," (J. Vet Diag. Invest. vol. 23, pp. 68-76, EDAT, Jan. 11, 2011).
Greer et al., "Necrotizing meningoencephalitis of pug dogs associates with dog leukocyte antigen class II and resembles acute variant forms of multiple sclerosis," (Tissue Antigens, vol. 76, pp. 110-118, 2010).
Safra et al. "Expanded dog leukocyte antigen (DLA) single nucleotide polymorphism (SNP) genotyping reveals spurious class II associations." (Veterinary Journal, vol. 189, pp. 220-226, 2011).
Barber et al. "Identification of risk loci for necrotizing meningoencephalitis in pug dogs," The Am. Genetic Association, J. of Heredity, vol. 102, S1, pp. S40-S46, EDAT: Aug. 24, 2011).
Smith et al, "Random prime labeling of DNA," (Methods in Molecular Biology, vol. 18, pp. 445-447, 1993).
Abitbol et al, "A canine arylsulfatase G (ARSG) mutation leading to a sulfatase deficiency is associated with neuronal ceroid lipofuscinosis," (PNAS, vol. 107, No. 33, pp. 14775-14780, Aug. 17, 2010)
Tacher et al. "Olfactory receptor sequence polymorphism within and between breeds of dogs," (J. of Heredity, vol. 96, No. 7, pp. 812-816, 2005).
Rothstein et al. "Chronic inhibition of superoxide dismutase produces apoptotic death of spinal neurons." (1994) PNAS USA 91: pp. 4155-4159.
NEB Catalog (1996/1997), pp. 29-32.

* cited by examiner

*Primary Examiner* — Jeanine A Goldberg
(74) *Attorney, Agent, or Firm* — The Noblitt Group, PLLC

(57) ABSTRACT

The present invention provides method of classifying a subject into a necrotizing meningoencephalitis (NME) disease risk group. The method may include assessing the presence of one or more marker (e.g., SNPs or risk loci) in a sample from the subject. For example, detection of the presence of one or more markers that are associated with an increased risk of NME can indicate that the subject should be classified into a risk group.

8 Claims, 13 Drawing Sheets

Specification includes a Sequence Listing.

FIG. 1

| Canine SNP | Chr | Pos | $A_R$ | $A_{NR}$ |
|---|---|---|---|---|
| BICF2P178662 | 12 | 5166878 | A | G |
| BICF2S23225431 | 12 | 5217389 | G | A |
| BICF2P22942 | 12 | 5227499 | G | A |
| BICF2P194998 | 12 | 5275229 | A | T |
| rs8856589 | 12 | 5622709 | C | A |
| BICF2P574765 | 12 | 5710832 | A | G |
| BICF2P1186632 | 12 | 5734305 | A | G |
| BICF2P1185629 | 12 | 5791672 | G | A |
| BICF2P540937 | 12 | 5829667 | A | G |
| rs9189886 | 12 | 5843592 | G | C |
| rs9006653 | 12 | 5916360 | A | G |
| BICF2P1200278 | 12 | 5931001 | G | A |
| rs9125534 | 12 | 5935549 | A | G |
| BICF2S23322760 | 12 | 5992526 | A | G |
| rs8760645 | 12 | 6024841 | T | A |
| rs9245050 | 12 | 6028685 | G | A |
| BICF2P863589 | 12 | 6059850 | A | G |
| BICF2P1115728 | 12 | 6064245 | C | A |
| BICF2P1254053 | 12 | 6149213 | G | A |
| BICF2P402427 | 12 | 6160615 | A | C |
| rs8694179 | 12 | 6164202 | A | G |
| BICF2P459960 | 12 | 6184107 | G | A |
| BICF2S22951431 | 12 | 6197313 | A | C |
| BICF2P1261424 | 12 | 6200280 | G | A |
| rs9120943 | 12 | 6218850 | A | G |
| rs9077055 | 12 | 6238545 | A | G |
| rs8677516 | 12 | 6257019 | G | A |
| BICF2P608380 | 12 | 6289014 | G | A |
| rs9132539 | 12 | 6299459 | A | G |
| BICF2P1340012 | 12 | 6311277 | C | A |
| BICF2P1211546 | 12 | 6320910 | A | G |
| BICF2P738783 | 12 | 6342204 | A | C |
| BICF2P1313789 | 12 | 6653816 | A | G |
| BICF2P639740 | 12 | 6686088 | G | A |
| BICF2P535495 | 12 | 6793393 | A | G |
| BICF2P1380652 | 12 | 6809061 | A | G |
| rs8957837 | 12 | 6822596 | C | G |
| BICF2P1462329 | 12 | 6832252 | A | G |

FIG. 2

| Canine SNP | Chr | Pos | $A_R$ | $A_{NR}$ |
|---|---|---|---|---|
| BICF2S23516667 | 8 | 31971609 | A | G |

METHODS OF ASSESSING A RISK OF DEVELOPING NECROTIZING MENINGOENCEPHALITIS

CROSS-REFERENCES TO RELATED APPLICATIONS

This application is a Continuation of U.S. patent application Ser. No. 14/713,134, filed on May 15, 2015, which claims the benefit of U.S. Provisional Patent Application No. 61/993,399, filed on May 15, 2014, and is a Continuation-in-Part of U.S. patent application Ser. No. 13/905,109, filed on May 29, 2013, which claims the benefit of U.S. Provisional Patent Application 61/652,732, filed on May 29, 2012, and this application is a Continuation-in-Part of U.S. patent application Ser. No. 13/698,907, which was the National Stage of International Application No. PCT/US11/37262, filed on Mar. 8, 2013, which claims the benefit of U.S. Provisional Patent Application 61/346,309, filed on May 19, 2010, and incorporates the disclosure of each application herein by reference in their entirety.

BACKGROUND OF THE INVENTION

Necrotizing meningoencephalitis (NME) is a non-suppurative inflammatory disorder of the canine central nervous system. Overrepresented in Pug dogs, NME also occurs in other small breeds including the Maltese and Chihuahua. The etiology of NME is unknown but non-Mendelian inheritance has been demonstrated in Pug dogs, suggesting a role for genetic risk factors in the development of disease.

Necrotizing meningoencephalitis (NME) is an idiopathic inflammatory disorder of the central nervous system (CNS) that primarily affects young to middle aged toy breed dogs. NME has known non-Mendelian inheritance that shares clinical similarities with atypical variants of multiple sclerosis in humans. Inflammation in NME is characterized by mixed mononuclear cell infiltrates within the cerebral hemispheres and cortical leptomeninges with common clinical signs including seizures, depression, behavior change, circling and visual deficits. Similar to severe non-prototypical forms of multiple sclerosis (MS) such as Marburg variant, NME is overrepresented in females, is rapidly progressive, and often carries a grave prognosis despite aggressive immunosuppressive treatment.

NME initially was identified in Pug dogs in the late 1960s and is known to have a strong familial association in this breed. Purebred dog populations provide a unique opportunity for mapping genetic traits and recent technological developments have made it possible to leverage dogs as a model for the study of human genetic disease. Dogs and humans share similar physiology with over half of the known canine diseases having a similar phenotype to analogous human diseases. An evaluation of canine NME, a disorder having clinical similarities to atypical, fulminant variants of MS in humans, is needed for identifying at risk and affected dogs, allowing development of targeted therapy and identifying similar genetic factors that are associated with the development of rapidly progressive MS in people.

Whether it is a human population or a canine population, the standard for measuring genetic variation among individuals in a population is the haplotype, which is the ordered combination of polymorphisms in the sequence of each form of a gene that exists in the population. Because haplotypes represent the variation across each form of a gene, they provide a more accurate and reliable measurement of genetic variation than individual polymorphisms. For example, while specific variations in gene sequences have been associated with a particular phenotype such as disease susceptibility (Roses A D supra; Ulbrecht M et al. 2000 Am J Respir Crit Care Med 161: 469-74) and drug response (Wolfe C R et al. 2000 BMJ 320:987-90; Dahl B S 1997 Acta. Psychiatr. Scand. 96 (Suppl 391): 14-21), in many other cases an individual polymorphism may be found in a variety of genomic backgrounds, i.e., different haplotypes, and therefore shows no definitive coupling between the polymorphism and the causative site for the phenotype (Clark A G et al. 1998 Am J Hum Genet 63:595-612; Ulbrecht M et al. 2000 supra; Drysdale et al. 2000 PNAS 97:10483-10488). Thus, there is an unmet need for information on what haplotypes exist in the dog population that are associated with NME. Since canine NME is a disorder having clinical similarities to MS in humans, canine NME haplotype information would be useful in improving the efficiency and output of NME and MS diagnosis, prognosis, and the several steps in the drug discovery and development process, including target validation, identifying lead compounds, and early phase clinical trials of drugs for MS.

BRIEF SUMMARY OF THE INVENTION

The present technology may provide a test that classifies a subject into an NME disease risk group. The test may predict whether or not a subject will develop NME. The test may use methods involving receiving a sample from a subject, isolating nucleic acid from the sample, detecting one or more of the markers listed in Table 2 and classifying the subject into a cohort based upon the presence or absence of the marker. The marker may be directed directly such as by Sanger sequencing, pyrosequencing, SOLID sequencing, massively parallel sequencing, barcoded DNA sequencing, PCR, real-time PCR, quantitative PCR, microarray analysis of genomic DNA, restriction fragment length polymorphism analysis, allele specific ligation, and comparative genomic hybridization. Alternatively, the marker may be directed indirectly such as by microarray analysis of RNA, RNA in situ hybridization, RNAse protection assay, Northern blot, reverse transcription PCR, quantitative PCR, quantitative reverse transcription PCR, quantitative real-time reverse transcription PCR, reverse transcriptase treatment followed by direct sequencing, flow cytometry, immunohistochemistry, ELISA, Western Blot, immunoaffinity chromatography, HPLC, mass spectrometry, protein microarray analysis, PAGE analysis, isoelectric focusing, and 2D gel electrophoresis. The marker may be a marker that is associated with a high risk of developing NME and the subject is classified into a risk group comprising subjects with a high risk of developing NME if the marker is detected in the sample. The subject may be any animal including a dog such as a Pug Dog, Chihuahua, Maltese Terrier, West Highland White Terrier, Yorkshire Terrier, French Bulldog, and Pekingese.

Various embodiments of the present technology may be implemented through the use of kits comprising a first probe capable of detecting a first SNP selected from the group listed in Table 2, a second probe capable of detecting a second SNP selected from Table 2; and wherein the probes are associated with a microarray of 1000 or fewer elements. The first probe may be capable of detecting a SNP associated with a higher risk of developing NME, or the second probe may be capable of detecting a SNP associated with a lower risk of developing NME.

BRIEF DESCRIPTION OF THE FIGURES

FIG. 1 depicts the SNPs in DLA class II region on Chromosome 12, with alternative base as listed for $A_R$, the allele associated with NME risk, and $A_{NR}$, the non-risk allele;

FIG. 2 depicts the SNP in STYX region on Chromosome 8, with alternative base as listed for $A_R$, the allele associated with NME risk, and $A_{NR}$, the non-risk allele;

DETAILED DESCRIPTION OF THE INVENTION

Figure 3:
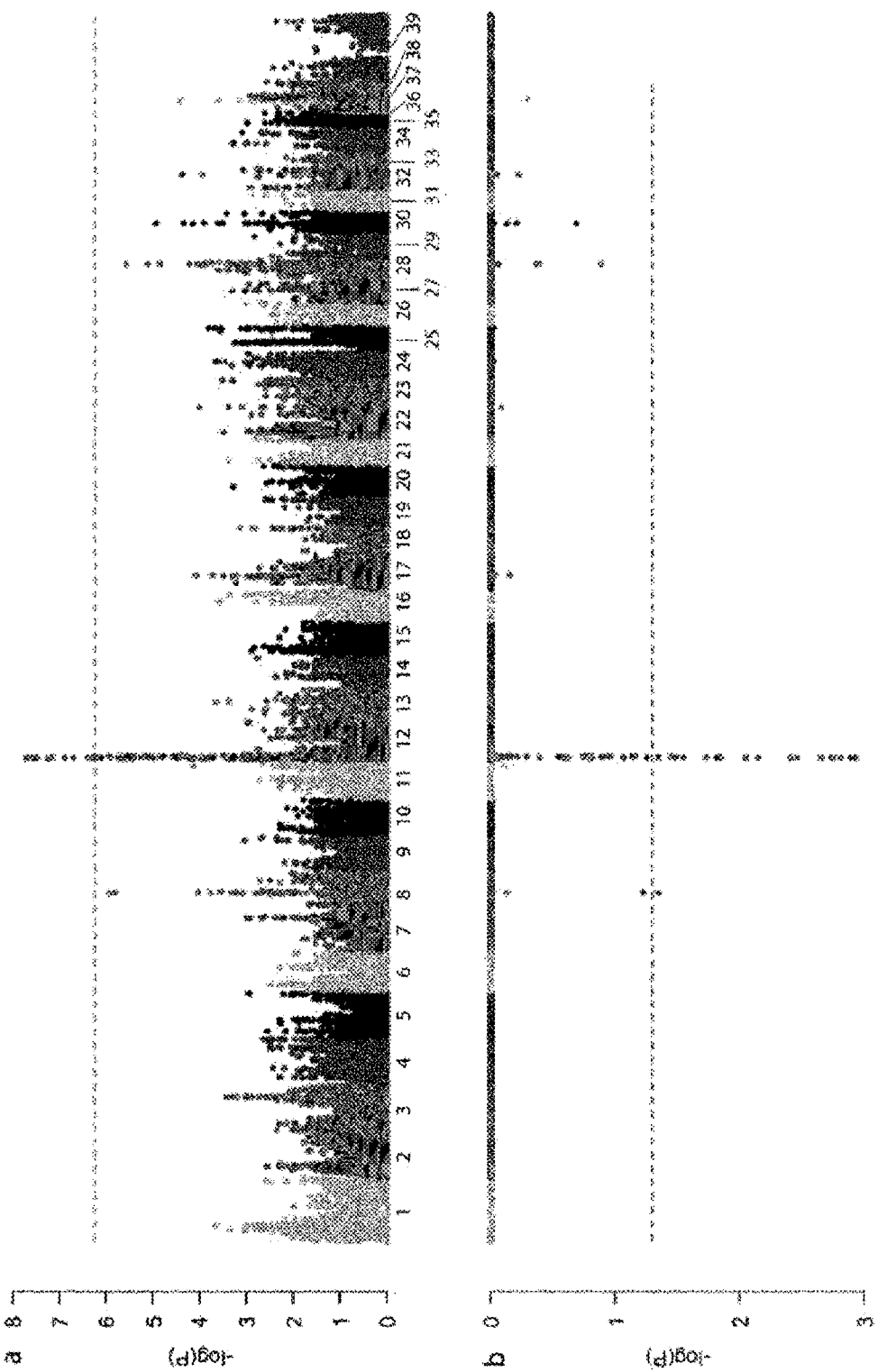
FIG. 3 depicts the genome-wide association results for 28 NME cases and 45 controls. (a) Fisher's exact tests were performed to compare SNP allele frequencies and negative log P values were plotted across the genome. The horizontal dotted line represents the threshold for significant association after Bonferroni correction of $-\log(P) > 6.24$ with a strong peak on chromosome 12 maintaining genome-wide significance. (b) MaxT 100,000 permutation testing was performed and negative log P values were plotted across the genome. The horizontal dotted line represents the threshold for significant association after permutation testing of $-\log(P) > 1.3$ with one SNP on chromosome 8 maintaining permuted significance.

The disclosure provides a method of assigning a subject to a necrotizing meningoencephalitis (NME) risk group in order to assess the likelihood of the subject being afflicted with the disease. This method can be employed to assess the risk at early stages of disease progression. The method includes providing a biological sample from the subject, detecting a marker in a biological sample, which can be a haplotype associated with NME and assigning the subject to the NME risk group based upon the presence or absence of the haplotype. The method involves directly or indirectly detecting the presence or absence of the marker. Multiple markers disclosed herein may be used in combination to improve the accuracy, including two or more, three or more, four or more, five or more, or ten or more of the markers may be used.

A haplotype refers to a segment of genomic DNA that is characterized by a specific combination of genetic markers (or alleles) arranged along the segment. A marker refers to a sequence characteristic of a particular allele. Detection of the disease also includes detection of the haplotype by any SNPs (single nucleotide polymorphisms) or other types of markers within the haplotype, but also indirectly through SNPs/markers outside the haplotype and leveraging linkage disequilibrium to identify carriers of the haplotype. Examining haplotypes rather than individual SNPs gives much stronger signal in detecting disease association. In addition, haplotypes can represent a combined effect of several sites along the same chromosome that cannot be detected when these sites are tested one by one. In the present technology, in addition to determining a patient's relative risk for NME, the diagnosis may include prescribing therapeutic regimens to treat, prevent or delay onset of NME.

A haplotype may be any combination of one or more closely linked alleles inherited as a unit with little genetic shuffling across generations. An allele includes any form of a particular nucleic acid that may be recognized as a form of the particular nucleic acid on account of its location, sequence, polymorphism, epigenetic modification or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene sequence, whether alone or in combination. The presence or absence of an allele may be detected through the use of any process through which a specific nucleic acid molecule may be detected, including direct and indirect methods of detecting the presence or absence of the specific nucleic acid. Different alleles may, but need not, result in detectable differences in gene expression or protein functions. An allele of a gene may or may not encode proteins or peptides. Different alleles may differ in expression level, pattern, temporal or spatial specificity, and expression regulation. In the case of encoded proteins, the protein from different alleles may or may not be functional. Further, the protein may be gain-of-function, loss-of-function, or with altered function. An allele may also be called a mutation or a mutant. An allele may be compared to another allele that may be termed a wild type form of an allele. In some cases, the wild type allele is more common than the mutant.

Different combinations of polymorphisms may also be called haplotypes. The polymorphism may be a single nucleotide polymorphism. The genetic sequences of different individuals are remarkably similar. When the chromosomes of two humans are compared, their DNA sequences can be identical for hundreds of bases. But at about one in every 1000 to 1,200 bases, on average, the sequences will differ. As such, one individual might have an A at that location, while another individual has a G, or a person might have extra bases at a given location or a missing segment of DNA. Differences in individual bases are the most common type of genetic variation. These genetic differences are known as single nucleotide polymorphisms (SNPs) (supra). SNPs act as markers to locate genes in DNA. Given the relatively close spacing between these SNPs, SNPs are typically inherited in blocks.

The difference of a single genetic variance such as a SNP can delineate a distinct haplotype. A "SNP haplotype block" or "haplotype block" is a nucleic acid sequence containing a group of SNPs or polymorphisms that do not appear to recombine independently resulting in reduced genetic variability but are passed together from generation to generation in variable-length blocks. The combination of polymorphisms, haplotype patterns and haplotype blocks may be referred to as a "haplotype" or "haplotype structure" in a nucleic acid sequence of interest. For example, a haplotype can be a set of SNPs, alleles, or genetic markers on a single chromatid that are genetically linked and thus are likely to be inherited as a unit. "Linked", "linkage", or "allelic association" means the preferential association of a particular allele or genetic marker with a specific allele or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Haplotypes are the particular combinations of alleles observed in a population, and are regions over which there is a very small proportion (often less than 5%) of informative SNP pairs showing strong evidence of historical recombination. Haplotype patterns may be disrupted by forces other than recombination, such as, recurrent mutation, gene conversion, or simply genome assembly or genotyping errors, which accounts for the approximate 5% disruption. Generally, directly genotyping pedigrees and using molecular methods, such as allele-specific polymerase chain reaction (AS-PCR) and somatic cell hybrids, in combination with genotyping can unambiguously assign alleles to chromosomes and thus determine the haplotypes. Other methods of determining or constructing a haplotype include statistical inference using various algorithms to process genotype data. Further, two or more alleles likely to be inherited as a unit is termed a haplotype block. Typically, a haplotype block refers to a chromosome region of high linkage disequilibrium and low haplotype diversity, and are regions of low recombination flanked by recombination hotspots (e.g., Cardon, L R and Abecasis, G R, *Trends in Genetics,* 19(3):135-140 (2003)).

As described above, two or more alleles likely to be inherited as a unit may be termed a haplotype block. When one or more haplotype blocks are associated with a phenotypic trait, the haplotype block serves as a genetic marker represented by a genetic locus comprising one or more linked genetic variations that would be inherited as a unit more frequently than not in an individual having the associated phenotypic trait. Therefore the haplotype block, and/or the haplotype may also be used to identify individuals from biological samples for traits of interest. The haplotype block may, in turn, be used to identify individual polymorphic sites, or candidate disease-associated genes for developing therapeutics and diagnostics. In the present invention, a DLA class II region comprising SEQ ID NO. 1 is identified as having significant association to the risk of NME. The haplotype comprising SEQ ID NO. 1 may be further described using 35 tag SNPs, or 19 haplotype blocks, some of which can be detected by one or more tag SNPs as disclosed. As disclosed in the present invention, the haplotype, the tag SNPs and the haplotype blocks are markers or marker combinations that can be used for NME identification and treatment. The present invention also discloses a STYX region containing a haplotype associated to the risk of NME genes for developing therapeutics and diagnostics.

Other additional markers that may also be used are those genetically linked to the markers disclosed herein. These additional markers, such as, SNPs or other polymorphic markers, are in close enough proximity to have a statistically significant association with the marker disclosed herein. Such statistically significant association may be defined by linkage disequilibrium, and the subject may be placed into a group either at higher or lower risk for NME depending on the presence of the additional marker, or a close isoform thereof, that is closely linked to higher or lower risk indicating markers.

Examples of methods for detecting the haplotype blocks are described herein and other suitable methods are well known to those of skill in the art. Suitable methods for detecting haplotypes in a sample include sequence analysis, hybridization analysis using a nucleic acid probe such DNA or RNA (e.g., Northern analysis, Southern analysis, dot blot analysis), and restriction digestion, genotyping the tag SNP(s) of the haplotype in each haplotype block.

In the methods of the invention, a sample can be obtained from the individual and used in the methods to detect the presence of the haplotype blocks. The haplotype block can be detected in any sample obtained from the individual that comprises the individual's DNA. For example, a haplotype block can be detected in a tissue sample (e.g., skin, muscle, organ, placenta), a cell sample (e.g., fetal cells), a fluid sample (e.g., blood, amniotic fluid, cerebrospinal fluid, urine, lymph) and any combination thereof. Methods of obtaining such samples or extracting nucleic acid from such samples are known to those of skill in the art.

The detection of the haplotype block in the individual can be compared to a control. Suitable controls for use in the methods provided herein are apparent to those of skill in the art. For example, a suitable control can be established by assaying one or more subjects which do not have NME. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

Various parameters may be used to assess how accurately the presence or absence of a marker signifies a particular physiological or cellular characteristic. Such parameters include a positive likelihood ratio, negative likelihood ratio, odds ratio, and/or hazard ratio. When a SNP haplotype block is identified by a SEQ ID NO, a set of at least two SNPs that are associated with an allele of a gene are grouped together in a linkage unit or block. In one embodiment of the present invention, the presence of SNPs detected in a given haplotype block disclosed herein in a dog is associated with a greater risk that the dog will develop NME, if it has not yet shown symptoms of NME; whereas the absence of SNPs detected in a given haplotype block disclosed herein in a dog is associated with a lesser risk that the dog will develop NME. A nucleic acid may be termed to be specific to a SNP haplotype block or specific to a SNP within a haplotype block. A nucleic acid specific to a haplotype block or a SNP within a haplotype block contains sequence that is complementary to one of the double stranded nucleic acid sequence of at least one SNP that is grouped within that haplotype block. Such nucleic acids may be complementary to a SNP that is associated with the nucleotide sequence in the linkage unit or block or any other SNP associated within the haplotype identified by the SNP haplotype block.

In various embodiments, the present technology provides a combination of markers comprising one or more haplotype blocks for identifying NME in canines. The haplotype blocks may be in a DLA class II region of canine chromosome 12, wherein the DLA class II region comprises sequence having at least 80%, more preferably 90%, still more preferably 95%, 96%, 97%, 98%, 99%, 99.5% or 99.9% sequence identity with SEQ ID NO. 1, wherein SEQ ID NO.1 has a start-end position from 4713000 to 8834700. The one or more haplotype blocks is selected from the group consisting of any one of haplotype blocks 1-19 and any combination thereof in Table 3. Further, the DLA class II region of chromosome 12 comprising the nucleic acid sequence of SEQ ID No. 1 may be defined by one or more tagging SNPs. The one or more tagging SNPs is selected from the group consisting of nucleic acid variation at position 5166878=A or G, 5217389=G or A, 5227499=G or A, 5275229=A or T, 5622709=C or A, 5710832=A or G, 5734305=A or G, 5791672=G or A, 5829667=A or G, 5843592=G or C, 5916360=A or G, 5931001=G or A, 5935549=A or G, 5992526=A or G, 6024841=T or A, 6028685=G or A, 6059850=A or G, 6064245=C or A, 6149213=G or A, 6160615=A or C, 6164202=A or G, 6184107=G or A, 6197313=A or C, 6200280=G or A, 6218850=A or G, 6238545=A or G, 6257019=G or A, 6289014=G or A, 6299459=A or G, 6311277=C or A, 6320910=A or G, 6342204=A or C, 6653816=A or G, 6686088=G or A, 6793393=A or G, 6809061=A or G, 6832252=A or G, and 8822596=C or G, for which 5166878=A, 5217389=G, 5227499=G, 5275229=A, 5622709=C, 5710832=A, 5734305=A, 5791672=G, 5829667=A, 5843592=G, 5916360=A, 5931001=G, 5935549=A, 5992526=A, 6024841=T, 6028685=G, 6059850=A, 6064245=C, 6149213=G, 6160615=A, 6164202=A, 6184107=G, 6197313=A, 6200280=G, 6218850=A, 6238545=A, 6257019=G, 6289014=G, 6299459=A, 6311277=C, 6320910=A, 6342204=A, 6653816=A, 6686088=G, 6793393=A, 6809061=A, 6832252=A and 8822596=C are risk alleles associated with developing Necrotizing Meningoencephalitis; wherein the two or more risk alleles are in linkage disequilibrium with one another.

In one example, the combination of markers comprising one or more haplotype blocks in a DLA class II region of canine chromosome 12 contains one or more haplotype blocks that is selected from the group consisting of haplotype blocks 4-8 and 19, and any combination thereof in Table 3. For example, the haplotype block 4 can be identified by one or more tagging SNP selected from the group consisting of nucleic acid variations at position 5166878=A or G, 5217389=G or A, 5227499=G or A, and 5275229=A or T; wherein 5166878=A, 5217389=G, 5227499=G, and 5275229=A are risk alleles associated with developing Necrotizing Meningoencephalitis. The haplotype block 5 can be identified by a tagging SNP having nucleic acid variations at position 5622709=C or A; wherein 5622709=C is a risk allele. The haplotype block 6 can be identified by one or more tagging SNP selected from the group consisting of nucleic acid variations at position 5710832=A or G, 5734305=A or G, 791672=G or A, 5829667=A or G, 5843592=G or C, 5916360=A or G, 5931001=G or A, 5935549=A or G, 5992526=A or G, 6024841=T or A, 6028685=G or A, 6059850=A or G, and 6064245=C or A; wherein 5710832=A, 5734305=A, 5791672=G, 5829667=A, 5843592=G, 5916360=A, 5931001=G, 5935549=A, 5992526=A, 6024841=T, 6028685=G, 6059850=A, and 6064245=C are risk alleles. The haplotype block 7 is identified by one or more tagging SNP selected from the group consisting of nucleic acid variations at position 6149213=G or A, 6160615=A or C, 6164202=A or G, 6184107=G or A, 6197313=A or C, 6200280=G or A, 6218850=A or G, 6238545=A or G, 6257019=G or A, 6289014=G or A, 6299459=A or G, 6311277=C or A, 6320910=A or G, 6342204=A or C; wherein 6149213=G, 6160615=A, 6164202=A, 6184107=G, 6197313=A, 6200280=G, 6218850=A, 6238545=A, 6257019=G, 6289014=G, 6299459=A, 6311277=C, 6320910=A, and 6342204=A are risk alleles associated with developing Necrotizing Meningoencephalitis. The haplotype block 8 is identified by one or more tagging SNP selected from the group consisting of nucleic acid variations at position 6653816=A or G, 6686088=G or A, 6793393=A or G, 6809061=A or G, 6832252=A or G, wherein 6653816=A or G, 6686088=G or A, 6793393=A or G, 6809061=A or G, 6832252=A or G are risk alleles. The haplotype block 19 is identified by a tagging SNP having nucleic acid variations at position 8822596=C or G; wherein 8822596=C is a risk allele associated with developing Necrotizing Meningoencephalitis.

The combination of markers for identifying NME in canine, which comprises one or more haplotype blocks in a DLA class II region of canine chromosome 12, having a start-end position from about 4713000 to about 8834700, may further comprise a haplotype block in STYX region of chromosome 8, wherein the STYX region comprises sequence having at least 80%, more preferably 90%, still more preferably 95%, 96%, 97%, 98%, 99%, 99.5% or 99.9% sequence identity with SEQ ID No. 2, wherein SEQ ID No. 2 has a start-end position from 31736000 to 32225100. This STYX region of chromosome 8 comprises a tagging SNP having nucleic acid variation at position 31971609=A or G, wherein 31971609=A is a risk allele associated with developing Necrotizing Meningoencephalitis.

The combination of markers for identifying NME in canine, which comprises one or more haplotype blocks in a DLA class II region of canine chromosome 12, having a start-end position from about 4713000 to about 8834700, may further comprise a HLA-DPB1 single base deletion variant at position 5608903, wherein the deletion variant comprising SEQ ID NO.26 is associated with developing Necrotizing Meningoencephalitis. The haplotype block 7 can be identified by the HLA-DPB1 single base deletion variant comprising SEQ ID NO.26. The haplotype block 7 may be further identified by the HLA-DPB1 single base deletion variant comprising SEQ ID NO.26 and a tagging SNP comprising nucleic acid variations at position 5622709=C or A; wherein 5622709=C is a risk allele associated with developing Necrotizing Meningoencephalitis. The one or more haplotype blocks of the combination of markers in a DLA class II region of canine chromosome 12 may be detected by genotyping using PCR, sequencing, hybridization, restriction digestion, or any combination thereof. The combinations of the markers as disclosed herein are suitable for canine species selected from a group consisting of Pug, Chihuahua, West Highland White Terrier, Pekingese, Labrador Retriever, Golden Retriever, Beagle, German Shepherd, Dachshund, Yorkshire Terrier, Boxer, Poodle, Shih Tzu, Miniature Schnauzer, Pomeranian, Cocker Spaniel, Rottweiler, Bulldog, Shetland Sheepdog, Boston Terrier, Miniature Pinscher, Maltese, German Shorthaired Pointer, Doberman Pinscher, Siberian Husky, Pembroke Welsh Corgi, Basset Hound, Bichon Frise, and other currently recognized and or yet to be recognized breeds.

The present invention further provides a combination of markers for identifying NME in canine which comprises a HLA-DPB1 single base deletion variant at position 5608903 of canine chromosome 12, and the deletion variant comprising SEQ ID NO.26 is associated with developing Necrotizing Meningoencephalitis. In addition to a HLA-DPB1 single base deletion variant at position 5608903 of canine chromosome 12, such a combination of markers further comprises one or more tagging SNPs selected from the group consisting of nucleic acid variations at position 5166878=A or G, 5217389=G or A, 5227499=G or A, 5275229=A or T, 5622709=C or A, 5710832=A or G, 5734305=A or G, 5791672=G or A, 5829667=A or G, 5843592=G or C, 5916360=A or G, 5931001=G or A, 5935549=A or G, 5992526=A or G, 6024841=T or A, 6028685=G or A, 6059850=A or G, 6064245=C or A, 6149213=G or A, 6160615=A or C, 6164202=A or G, 6184107=G or A, 6197313=A or C, 6200280=G or A, 6218850=A or G, 6238545=A or G, 6257019=G or A, 6289014=G or A, 6299459=A or G, 6311277=C or A, 6320910=A or G, 6342204=A or C, 6653816=A or G, 6686088=G or A, 6793393=A or G, 6809061=A or G, 6832252=A or G, and 8822596=C or G; for which, 5166878=A, 5217389=G, 5227499=G, 5275229=A, 5622709=C, 5710832=A, 5734305=A, 5791672=G, 5829667=A, 5843592=G, 5916360=A, 5931001=G, 5935549=A, 5992526=A, 6024841=T, 6028685=G, 6059850=A, 6064245=C, 6149213=G, 6160615=A, 6164202=A, 6184107=G, 6197313=A, 6200280=G, 6218850=A, 6238545=A, 6257019=G, 6289014=G, 6299459=A, 6311277=C, 6320910=A, 6342204=A, 6653816=A, 6686088=G, 6793393=A, 6809061=A, 6832252=A; and 8822596=C are risk alleles associated with developing Necrotizing Meningoencephalitis; wherein the two or more risk alleles are in linkage disequilibrium with one another.

The present invention also provides a method of classifying a subject to an NME disease risk group, which comprises the steps of receiving a nucleic acid-containing sample from the subject; detecting the presence of a combination of markers comprising one or more haplotype blocks and tagging SNPs in a DLA class II region of canine chromosome 12 comprising sequences having at least 80%, more preferably 90%, still more preferably 95%, 96%, 97%, 98%, 99%, 99.5% or 99.9% sequence identity with SEQ ID No. 1, wherein SEQ ID No.1 has start-end position from 4713000 to 8834700; and classifying the subject into a risk group based upon the presence of at least one haplotype block, or classifying the subject into a non-risk group based upon the absence of any haplotype block. In the general method, the one or more haplotype blocks is selected from the group consisting of haplotype blocks 1-19 and any combination thereof in Table 3. Further, the one or more tagging SNPs in the general method is selected from the group consisting of nucleic acid variation at position 5166878=A or G, 5217389=G or A, 5227499=G or A, 5275229=A or T, 5622709=C or A, 5710832=A or G, 5734305=A or G, 5791672=G or A, 5829667=A or G, 5843592=G or C, 5916360=A or G, 5931001=G or A, 5935549=A or G, 5992526=A or G, 6024841=T or A, 6028685=G or A, 6059850=A or G, 6064245=C or A, 6149213=G or A, 6160615=A or C, 6164202=A or G, 6184107=G or A, 6197313=A or C, 6200280=G or A, 6218850=A or G, 6238545=A or G, 6257019=G or A, 6289014=G or A, 6299459=A or G, 6311277=C or A, 6320910=A or G, 6342204=A or C, 6653816=A or G, 6686088=G or A, 6793393=A or G, 6809061=A or G, 6832252=A or G, and 8822596=C or G, for which 5166878=A, 5217389=G, 5227499=G, 5275229=A, 5622709=C, 5710832=A, 5734305=A, 5791672=G, 5829667=A, 5843592=G, 5916360=A, 5931001=G, 5935549=A, 5992526=A, 6024841=T, 6028685=G, 6059850=A, 6064245=C, 6149213=G, 6160615=A, 6164202=A, 6184107=G, 6197313=A, 6200280=G, 6218850=A, 6238545=A, 6257019=G, 6289014=G, 6299459=A, 6311277=C, 6320910=A, 6342204=A, 6653816=A, 6686088=G, 6793393=A, 6809061=A, 6832252=A; and 8822596=C are risk alleles associated with developing Necrotizing Meningoencephalitis; wherein the two or more risk alleles are in linkage disequilibrium with one another. The general method provided herein is suitable for canine species selected from a group consisting of Pug, Chihuahua, West Highland White Terrier, Pekingese, Labrador Retriever, Golden Retriever, Beagle, German Shepherd, Dachshund, Yorkshire Terrier, Boxer, Poodle, Shih Tzu, Miniature Schnauzer, Pomeranian, Cocker Spaniel, Rottweiler, Bulldog, Shetland Sheepdog, Boston Terrier, Miniature Pinscher, Maltese, German Shorthaired Pointer, Doberman Pinscher, Siberian Husky, Pembroke Welsh Corgi, Basset Hound, Bichon Frise, and other currently recognized and or yet to be recognized breeds.

One aspect of the present invention provides an isolated nucleic acid molecule selected from the group consisting of: (a) an isolated nucleic acid molecule comprising the sequence of SEQ ID NO:1; (b) an isolated nucleic acid molecule comprising the sequence of SEQ ID NO:2; (c) an isolated nucleic acid molecule comprising a segment of SEQ ID NO:1; (d) an isolated nucleic acid molecule comprising a segment of SEQ ID NO:2; and, (e) an isolated nucleic acid molecule which is complementary to the isolated nucleic acid molecule of (a), (b), (c), and (d); wherein the isolated nucleic acid molecule comprises one or more markers selected from the group consisting of SNP alleles, haplotype blocks, or gene indel variants that are associated with a risk or non-risk of developing Necrotizing Meningoencephalitis in a subject. The marker is selected from the group consisting of SNPs as listed in FIG. 1 and FIG. 2, haplotype blocks listed in Table 3 and Table 4, and gene indel variants in the DLA II region of canine Chromosome 12 and the STYX region of Chromosome 8.

In some examples, said isolated nucleic acid molecule comprises two or more single nucleotide polymorphisms (SNPs) as listed in FIG. 1 and FIG. 2, wherein the two or more SNPs are in linkage disequilibrium with one another. In one example, the gene indel variant is an HLA-DPB1 deletion variant represented by SEQ ID NO: 26, and this deletion allele of HLA-DPB1 is associated with a risk of developing Necrotizing Meningoencephalitis. In another example, the one or more SNPs having loci in the sequence of SEQ ID NO: 1 and SEQ ID NO: 2 are selected from a group consisting of nucleotide variations: 5166878=A or G; 5217389=G or A; 5227499=G or A; 5275229=A or T; 5622709=C or A; 5710832=A or G; 5734305=A or G; 5791672=G or A; 5829667=A or G; 5843592=G or C; 5916360=A or G; 5931001=G or A; 5935549=A or G; 5992526=A or G; 6024841=T or A; 6028685=G or A; 6059850=A or G; 6064245=C or A; 6149213=G or A; 6160615=A or C; 6164202=A or G; 6184107=G or A; 6197313=A or C; 6200280=G or A; 6218850=A or G; 6238545=A or G; 6257019=G or A; 6289014=G or A; 6299459=A or G; 6311277=C or A; 6320910=A or G; 6342204=A or C; 6653816=A or G; 6686088=G or A; 6793393=A or G; 6809061=A or G; 6832252=A or G; 8822596=C or G, on canine Chromosome 12 at the indicated position; and 31971609=A or G on canine Chromosome 8 at the indicated position. Specifically, the one or more SNPs that are associated with a risk of developing Necrotizing Meningoencephalitis are selected from a group consisting of nucleotide: 5166878=A; 5217389=G; 5227499=G; 5275229=A; 5622709=C; 5710832=A; 5734305=A; 5791672=G; 5829667=A; 5843592=G; 5916360=A; 5931001=G; 5935549=A; 5992526=A; 6024841=T; 6028685=G; 6059850=A; 6064245=C; 6149213=G; 6160615=A; 6164202=A; 6184107=G; 6197313=A; 6200280=G; 6218850=A; 6238545=A; 6257019=G; 6289014=G; 6299459=A; 6311277=C; 6320910=A; 6342204=A; 6653816=A; 6686088=G; 6793393=A; 6809061=A; 6832252=A; 8822596=C, on canine Chromosome 12 at the indicated position; and 31971609=A on canine Chromosome 8 at the indicated position. In still another example, the one or more haplotype blocks that are associated with a risk of developing Necrotizing Meningoencephalitis are selected from a group consisting of sequences represented by: SEQ ID NO: 3 at position 4713392-4821633, SEQ ID NO:4 at position 4836721-4923170, SEQ ID NO:5 at position 4938082-5088561, SEQ ID NO:6 at position 5108726-5364188, SEQ ID NO:7 at position 5491709-5672682, SEQ ID NO:8 at position 5710832-6078099, SEQ ID NO:9 at position 6149213-6342204, SEQ ID NO:10 at position 6492201-6982375, SEQ ID NO:11 at position 6992493-7270218, SEQ ID NO:12 at position 7338759-7350261, SEQ ID NO:13 at position 7384390-7643147, SEQ ID NO:14 at position 7725530-7830733, SEQ ID NO:15 at position 7927872-7944953, SEQ ID NO:16 at position 7950821-8158994, SEQ ID NO:17 at position 8208369-8265940, SEQ ID NO:18 at position 8327142-8386063, SEQ ID NO:19 at position 8429601-8533350, SEQ ID NO:20 at position 8546686-8713747, SEQ ID NO:21 at position 8719506-8834652, on canine Chromosome 12; and SEQ ID NO: 22 at position 31,736,206 to 31,795,128, SEQ ID NO: 23 at position 31,866,373 to 31,883,390, SEQ ID NO: 24 at position 31,971,609 to 32,009,283, and SEQ ID NO: 25 at position 32,183,184 to 32,225,068, on canine Chromosome 8. In some examples, the isolated nucleic acid molecule may be in the form of a probe or primer, and the probe or primer hybridizes under stringent conditions to said isolated nucleic acid molecule of claim 1.

Another aspect of the present invention provides a method of classifying a subject to an NME disease risk group. The method comprises (1) receiving a nucleic acid-containing sample from the subject; (2) detecting the presence of one or more markers selected from the group consisting of one or more SNP alleles, haplotype blocks, and gene indel variants that are associated with a risk of developing Necrotizing Meningoencephalitis in the subject, wherein the SNP alleles, haplotype blocks, and gene indel variants are represented by nucleic acid segments in SEQ ID NO:1 and SEQ ID NO:2; and (3) classifying the subject into a risk group based upon the presence of at least one haplotype block, or classifying the subject into a non-risk group based upon the absence of any haplotype block. In one example of performing the general method, the one or more SNP alleles are selected from the group consisting of nucleotide: 5166878=A; 5217389=G; 5227499=G; 5275229=A; 5622709=C; 5710832=A; 5734305=A; 5791672=G; 5829667=A; 5843592=G; 5916360=A; 5931001=G; 5935549=A; 5992526=A; 6024841=T; 6028685=G; 6059850=A; 6064245=C; 6149213=G; 6160615=A; 6164202=A; 6184107=G; 6197313=A; 6200280=G; 6218850=A; 6238545=A; 6257019=G; 6289014=G; 6299459=A; 6311277=C; 6320910=A; 6342204=A; 6653816=A; 6686088=G; 6793393=A; 6809061=A; 6832252=A; 8822596=C, on canine Chromosome 12 at the indicated position; and 31971609=A on canine Chromosome 8 at the indicated position.

In another example of performing the general method, the one or more haplotype blocks are selected from the group consisting of sequences represented by: SEQ ID NO: 3 at position 4713392-4821633, SEQ ID NO:4 at position 4836721-4923170, SEQ ID NO:5 at position 4938082-5088561, SEQ ID NO:6 at position 5108726-5364188, SEQ ID NO:7 at position 5491709-5672682, SEQ ID NO:8 at position 5710832-6078099, SEQ ID NO:9 at position 6149213-6342204, SEQ ID NO:10 at position 6492201-6982375, SEQ ID NO:11 at position 6992493-7270218, SEQ ID NO:12 at position 7338759-7350261, SEQ ID NO:13 at position 7384390-7643147, SEQ ID NO:14 at position 7725530-7830733, SEQ ID NO:15 at position 7927872-7944953, SEQ ID NO:16 at position 7950821-8158994, SEQ ID NO:17 at position 8208369-8265940, SEQ ID NO:18 at position 8327142-8386063, SEQ ID NO:19 at position 8429601-8533350, SEQ ID NO:20 at position 8546686-8713747, SEQ ID NO:21 at position 8719506-8834652, on canine Chromosome 12; and SEQ ID NO: 22 at position 31,736,206 to 31,795,128, SEQ ID NO: 23 at position 31,866,373 to 31,883,390, SEQ ID NO: 24 at position 31,971,609 to 32,009,283, and SEQ ID NO: 25 at position 32,183,184 to 32,225,068, on canine Chromosome 8.

In yet another example of performing the general method, the marker is the gene indel variant HLA-DPB1 deletion variant represented by SEQ ID NO: 26.

Another aspect of the present invention provides a set of molecular probes used in assessing the risk of developing NME of a subject, which comprises a first probe capable of detecting a first marker selected from the group consisting of a SNP allele listed in FIG. 1 and FIG. 2, a haplotype block in Table 3 and Table 4, and an HLA-DPB1 deletion variant represented by SEQ ID NO: 26; and a second probe, different from the first probe, capable of detecting a second marker selected from the group consisting of a SNP allele listed in FIG. 1 and FIG. 2, a haplotype block in Table 3 and Table 4, and an HLA-DPB1 deletion variant represented by SEQ ID NO: 26, wherein the markers detected by the probes are associated with a high risk of developing NME and wherein the risk group comprises subjects with a high risk of developing NME.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived or any other chemical structure. Examples of such nucleic acids include miRNA, tRNA, siRNA, mRNA, cDNA, or genomic DNA sequences including complimentary sequences. Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker. In some embodiments, the detection of the marker may encompass the detection and/or determination of a change in copy number (e.g. copy number of a gene or other forms of nucleic acid) or in the detection of one or more translocations.

Examples of molecules encompassed by a marker represented by a particular sequence or structure include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following nonlimiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively, if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

In the present technology, the marker represented by a group of linked SNPs, "haplotype block," "haplotype", or gene products, including mRNA and protein, produced from the genes within the haplotype may be detected by a variety of methodologies or procedures that are well known in the art including, but not limited to, nucleic acid hybridization, antibody binding, activity assay, polymerase chain reaction (PCR), SI nuclease assay and via gene chip or microarray, as well as any other assay known in the art that may be used to detect the SNPs associated with a haplotype or the gene product produced from the gene of the haplotype including mRNA and protein. Hybridization of a SNP-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin interactions, salt bridges, hydrophobic interactions, chemical linkages, UV cross-linking baking, etc. SNP-specific oligonucleotides may be synthesized directly on the solid support or attached to the solid support subsequent to synthesis. Solid-supports suitable for use in detection methods of the disclosure include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the SNP-specific oligonucleotide or target nucleic acid. Detecting the nucleotide or nucleotide pair of interest may also be determined using a mismatch detection technique, including but not limited to the RNase protection method using riboprobes (Winter et al. (1985) *Proc. Natl. Acad. Sci. USA* 82:7575; Meyers et al. (1985) *Science* 230:1242) and proteins which recognize nucleotide mismatches, such as the *E. coli* mutS protein (Modrich (1991) *Ann. Rev. Genet.* 25:229-53). Alternatively, variant SNPs or variant alleles can be identified by single strand conformation polymorphism (SSCP) analysis (Orita et al. (1989) *Genomics* 5:874-9); Humphries et al. (1996) in MOLECULAR DIAGNOSIS OF GENETIC DISEASES, Elles, ed., pp. 321-340) or denaturing gradient gel electrophoresis (DGGE) (Wartell et al. (1990) *Nucl. Acids Res.* 18:2699706); Sheffield et al. (1989) *Proc. Natl. Acad. Sci. USA* 86:232-6).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/102087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruano et al. (1989) *Nucl. Acids Res.* 17:8392; Ruano et al. (1991) *Nucl. Acids Res.* 19:6877-82); WO 93/22456; Turki et al. (1995) 1. *Clin. Invest.* 95:1635-41). The haplotype for a gene of an individual may also be determined by hybridization of a nucleic acid sample containing one or both copies of the gene, mRNA, cDNA or fragment(s) thereof, to nucleic acid arrays and sub-arrays such as described in WO 95/112995. The arrays would contain a battery of SNP-specific or allele-specific oligonucleotides representing each of the polymorphic sites to be included in the haplotype.

Detecting the presence or absence of a marker disclosed herein or a close isoform thereof may be carried out either directly or indirectly by any suitable methodology. A variety of techniques are known to those skilled in the art (supra). All generally involve receiving a biological sample containing DNA or protein from the subject, and then detecting whether or not the marker or a close isoform thereof is present in the sample, and then determining the presence or absence of the marker in the sample.

The marker may be detected by any of a number of methods. Direct methods of detecting the presence of an allele include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, reverse transcription PCR or any combination of these; allele specific ligation; comparative genomic hybridization; or any other method that allows the detection of a particular nucleic acid sequence within a sample or enables the differentiation of one nucleic acid from another nucleic acid that differs from the first nucleic acid by one or more nucleotides.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent) stain, enzyme, or nonradioactive metal. Specific examples include, but are not limited to: fluorescein, biotin, digoxigenin, alkaline phosphates, biotin, streptavidin, 3H, 14C, 32P, 35S, or any other compound capable of emitting radiation, rhodamine, 4-(4'-dimethylamino-phenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

A sample for use in the methods herein may comprise a biological sample from a subject suspected of having or being at risk of having NME. The sample may be any suitable sample comprising nucleic acids used for various marker detection methods. For example, the sample may contain free or bound nucleic acids. The sample may contain whole cells which may be processed to make a cell lysate. In some embodiments, the marker detection methods may be performed on the cell lysate. In some embodiments, the nucleic acids may be extracted or further purified from the sample or the cell lysate for use with various marker detection methods.

Nucleic acids may include but need not be limited to RNA, cDNA, tRNA, mitochondrial DNA, plasmid DNA, siRNA, genomic DNA, or any other naturally occurring or artificial nucleic acid molecule. The sample may be any type of sample derived from the subject, including any body fluid or tissue that may contain one or more markers associated with the haplotype. Examples of sources of samples include, but are not limited to, biopsy or other in vivo or ex vivo analysis of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, urine, whole blood, serum, plasma, saliva, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples also include explants and primary and/or transformed cell cultures derived from patient tissues.

The subject may be any organism subject or susceptible to NME or MS including mammals, further including humans. The animal may be a canine such as a Pug Dog, Chihuahua, West Highland White Terrier, Pekingese, Labrador retriever, Golden retriever, Beagle, German shepherd, Dachshund, Yorkshire terrier, Boxer, Poodle, Shih tzu, Miniature schnauzer, Pomeranian, Cocker spaniel, Rottweiler, Bulldog, Shetland sheepdog, Boston terrier, Miniature pinscher, Maltese, German shorthaired pointer, Doberman pinscher, Siberian husky, Pembroke welsh corgi, Basset hound, Bichon frise, and other existing or non-existing breeds.

Examples of indirect methods of detection include any nucleic acid detection method including the following non-limiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a pyrophosphate upon nucleotide incorporation. An ATP sulfurylase enzyme converts pyrophosphate into ATP which in turn catalyzes the conversion of luciferin to oxyluciferin which results in the generation of visible light that is then detected by a camera or other sensor capable of capturing visible light.

In SOLID sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, the method may include the use of massively parallel sequencing, as detailed in U.S. Pat. Nos. 8,431,348 and 7,754,429, which are hereby incorporated by reference in their entirety.

Other methods used to assess expression and/or detect the presence/absence of a marker include the use of natural or artificial ligands having an affinity for a specific marker such that the ligands are capable of specifically binding the marker. For example, in some aspects, the natural and/or artificial ligands may comprise molecular probes that are capable of binding to the marker(s). Such ligands may also include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)2, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent) stain, enzyme, metal, or any other substance capable of aiding a machine or a human eye from differentiating a cell expressing a marker from a cell not expressing a marker. In other words, in some embodiments, the molecular probes may comprise a label, with said label being selected from the non-exclusive list provided above. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Other markers may also be used that are associated with the markers disclosed herein such as SNPs or other polymorphic markers that are in close enough proximity to have a statistically significant association with the marker disclosed herein (e.g., other markers in linkage disequilibrium with a marker disclosed herein). For example, if a marker or a close isoform thereof is detected in the subject, then the subject may be placed into a group either at higher or lower risk for NME depending on which marker or close isoform thereof is identified (i.e., a significant enough number of markers associated with a haplotype).

The disclosure also provides sets of molecular probes, as described above, for detection, including at least two probes capable of detecting, directly or indirectly, a marker disclosed herein associated with increased or decreased risk of NME, wherein the molecular probes are not associated with a microarray of greater than 1000 elements, a microarray with greater than 500 elements, a microarray with greater than 100 elements, a microarray with greater than 50 elements, or are not associated with a microarray. Such sets of two or more probes may include at least one probe capable of detecting, directly or indirectly, a marker disclosed herein associated with higher risk of developing NME and at least one other probe is capable of detecting, directly or indirectly, a marker disclosed herein associated with lower risk of developing NME. Moreover, as described above, the probes may comprise one or more labels selected from the non-exclusive list detailed above.

If a marker can be detected through expression level alteration, the expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include the identity of a cell as a particular cell including a particular normal or diseased cell type, the likelihood that one or more diseases is present or absent, the likelihood that a present disease will progress, remain unchanged, or regress, the likelihood that a disease will respond or not respond to a particular therapy, or any other disease outcome. Further examples include the likelihood that a cell will move, senesce, apoptose, differentiate, metastasize, or change from any state to any other state or maintain its current state.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis. Knowledge of the survival of the canine after diagnosis may be useful to inform veterinarians and/or owners about treatment such as immunosuppressive treatment, palliative treatment, or euthanasia. Additionally, knowledge of the risk of developing NME may inform breeders about whether to consider a canine as a potential candidate for breeding.

Determining whether or not the presence of an allele signifies a physiological or cellular characteristic may be assessed by any of a number of methods. The skilled artisan will understand that numerous methods may be used to select a marker or a plurality of markers that signifies a particular physiological or cellular characteristic. In diagnosing the presence of a disease, a threshold value may be obtained by performing the assay method on samples obtained from a population of patients having a certain type of disease (NME for example) and from a second population of subjects that do not have the disease. In assessing disease outcome or the effect of treatment, a population of patients, all of which may develop a disease such as NME, may be followed for a period of time. After the period of time expires, the population may be divided into two or more groups. For example, the population may be divided into a first group of patients who did develop NME and a second group of patients who did not develop NME. Examples of endpoints include occurrence of one or more symptoms of disease, death or other states to which the given disease may progress. If presence of the marker in a sample statistically aligns with one group relative to the other group, the subject from which the sample was derived may be assigned a risk of having the same outcome as the patient group that differentially displays the marker.

Other methods may be used to assess how accurately the presence or absence of a marker signifies a particular physiological or cellular characteristic. Such methods include a positive likelihood ratio, negative likelihood ratio, odds ratio, and/or hazard ratio. In the case of a likelihood ratio, the likelihood that the presence or absence of the marker would be found in a sample with a particular cellular or physiological characteristic is compared with the likelihood that the presence or absence of the marker would be found in a sample lacking the particular cellular or physiological characteristic.

An odds ratio measures effect size and describes the amount of association or non-independence between two groups. An odds ratio is the ratio of the odds of a marker being present or absent in one set of samples versus the odds of the marker being present or absent in the other set of samples. An odds ratio of 1 indicates that the event or condition is equally likely to occur in both groups. An odds ratio grater or less than 1 indicates that presence or absence of the marker is more likely to occur in one group or the other depending on how the odds ratio calculation was set up.

A hazard ratio may be calculated by estimate of relative risk. Relative risk is the chance that a particular event will take place. It is a ratio of the probability that an event such as development or progression of a disease will occur in samples in which a particular marker is present over the probability that the event will occur in samples in which the particular marker is absent. Alternatively, a hazard ratio may be calculated by the limit of the number of events per unit time divided by the number at risk as the time interval decreases. In the case of a hazard ratio, a value of 1 indicates that the relative risk is equal in both the first and second groups; a value greater or less than 1 indicates that the risk is greater in one group or another, depending on the inputs into the calculation.

EXAMPLES

Various embodiments of the present teachings can be illustrated in the following non-limiting examples. The following examples are illustrative, and are not intended to limit the scope of the claims.

Example 1

Methods and Material
Study Population:
Purebred Pug dogs were used for the case-control genome-wide association study. Cases were verified to have NME based on clinical history and independent evaluation of hematoxylin and eosin brain sections by a veterinary neuropathologist. Cases ranged in age from 4 to 84 months (mean=18 months, median=26 months) and consisted of 11 males and 19 females. Control dogs had no evidence of neurological or autoimmune disease, ranged in age from 5 to 204 months (mean=60 months, median=48 months) at the time of sample collection and consisted of 30 males and 38 females. Control dogs were followed for 18 months after sample collection to verify that they did not develop neurological or autoimmune disease.

Snp Genotyping:
Genomic DNA was isolated using the Qiagen Gentra Puregene® Tissue Kit or Qiagen DNeasy® Blood and Tissue Kit (Qiagen N. V., Venlo, Netherlands). SNP genotyping was performed with the Illumina CanineHD Genotyping BeadChip using the Illumina BeadArray reader (Illumina Inc., San Diego, Calif.) following the manufacturer's protocol. Genomic DNA was isolated from 30 Pug dogs with histopathologically confirmed NME and 68 healthy, control Pug dogs without evidence of neurological or autoimmune disease. Genomic DNA quality was assessed with 2% agarose gel electrophoresis and quantified with fluorometric dsDNA quantification. Genome-wide association of >100,000 SNPs was performed using the Illumina Canine Infinium® HD BeadChip, and SNPs were analyzed with PLINK (found on the web at pngu.mgh.harvard.edu/purcell/plink/) with a minor allele frequency of >5% and call rate of >98%.

Statistical Analysis:
Genotyping was performed on 98 dogs, including 30 NME cases and 68 controls. Genome-wide analysis was performed with PLINK (Purcell et al. 2007). Concordance on duplicate samples was 99.96%. Only samples with a call rate of >95% were included, resulting in analysis of 28 NME cases and 66 controls. A total of 172,115 SNPs were genotyped. Classic multidimensional scaling (Purcell et al. 2007) using a call rate of >97% and MAF of >0.10 was performed on 85,366 SNPs to determine population stratification, and 21 controls that were not clustered with the main population of dogs were excluded resulting in a final population of 28 NME cases and 45 controls for analysis. These 45 control dogs ranged in age from 5 to 204 months (mean=80 months, median=48 months). Prior to analysis, 7,324 SNPs were excluded for failure to reach the call rate threshold (>95%) and 81,001 SNPs were excluded for failure to reach the MAF threshold (>0.05). In total, 86,692 SNPs were used for analysis. Bonferroni correction was applied to account for multiple hypothesis testing with a resulting P value of $5.77 \times 10^{-7}$ across 86,692 SNPs for genome-wide significance. To further evaluate genome-wide significance, MaxT permutation testing (Purcell et al. 2007) of 100 000 permutations was applied.

Example 2

Identifying Disease-Associated SNPs Genome-Wide
Initial genotyping was performed on 30 NME cases and 68 controls across 172,115 SNPs. After quality filtering and exclusion of population outliers, analysis of 28 NME cases and 45 controls across 86,692 SNPs identified two disease-associated loci that reached genome-wide significance with correction for multiple hypothesis testing. The strongest association was on chromosome 12 where 35 SNPs within the DLA class II region reached genome-wide significance after Bonferroni correction (raw P value for Bonferroni genome-wide significance is $p<5.77 \times 10^{-7}$) with the highest SNP having an odds ratio of 16.1 (95% CI:4.7-55.5) (FIG. 3a and Table 1). FIG. 3 shows the genome-wide association results for 28 NME cases and 45 controls. In FIG. 3a, Fisher's exact tests were performed to compare SNP allele frequencies and negative log P values were plotted across the genome. The horizontal dotted line represents the threshold for significant association after Bonferroni correction of $-\log(P)>6.24$ with a strong peak on chromosome 12 maintaining genome-wide significance.

TABLE 1

SNPs with genome-wide significance after Bonferroni correction

| Canine SNP | Chr | Pos | $A_R/A_{NR}$ | $F_A/F_U$ | $P_{raw}$ | $P_{genome}$ | OR (95% CI) | Gene |
| --- | --- | --- | --- | --- | --- | --- | --- | --- |
| CF2P178662 | 12 | 5166878 | A/G | 0.95/0.52 | $2.36 \times 10^{-8}$ | 0.0020 | 16.1 (4.7-55.5) | RT1-Db2 |
| BICF2S23225431 | 12 | 5217389 | G/A | 0.86/0.36 | $2.87 \times 10^{-9}$ | 0.0002 | 10.5 (4.4-25) | RT1-Db2 |
| BICF2P22942 | 12 | 5227499 | G/A | 0.86/0.36 | $2.87 \times 10^{-9}$ | 0.0002 | 10.5 (4.4-25) | RT1-Db2 |
| BICF2P194998 | 12 | 5275229 | A/T | 0.79/0.30 | $8.59 \times 10^{-9}$ | 0.0007 | 8.7 (4-19.2) | |
| rs8856588 | 12 | 5622709 | C/A | 0.79/0.30 | $8.59 \times 10^{-9}$ | 0.0007 | 8.7 (4-19.2) | COL11A2 |
| BICF2P574765 | 12 | 5710832 | A/G | 0.79/0.30 | $8.59 \times 10^{-9}$ | 0.0007 | 8.7 (4-19.2) | bing4-a |
| BICF2P1186632 | 12 | 5734305 | A/G | 0.79/0.29 | $7.24 \times 10^{-9}$ | 0.0006 | 8.9 (4.1-19.7) | TAPBP |

TABLE 1-continued

SNPs with genome-wide significance after Bonferroni correction

| Canine SNP | Chr | Pos | $A_R/A_{NR}$ | $F_A/F_U$ | $P_{raw}$ | $P_{genome}$ | OR (95% CI) | Gene |
|---|---|---|---|---|---|---|---|---|
| BICF2P1185629 | 12 | 5791672 | G/A | 0.79/0.30 | $8.59 \times 10^{-9}$ | 0.0007 | 8.7 (4-19.2) | KIFC1 |
| BICF2P540937 | 12 | 5829667 | A/G | 0.79/0.32 | $6.27 \times 10^{-8}$ | 0.0054 | 7.9 (3.6-17.1) | CUTA |
| rs9189886 | 12 | 5843592 | G/C | 0.93/0.51 | $5.95 \times 10^{-8}$ | 0.0052 | 12.4 (4.1-37.3) | Syngap1 |
| rs9006653 | 12 | 5916360 | A/G | 0.79/0.33 | $8.07 \times 10^{-8}$ | 0.0070 | 7.5 (3.4-16.2) | Ppdpfb |
| BICF2P1200278 | 12 | 5931001 | G/A | 0.79/0.29 | $7.24 \times 10^{-9}$ | 0.0006 | 8.9 (4.1-19.7) | Ppdpfb |
| rs9125534 | 12 | 5935549 | A/G | 0.79/0.30 | $8.59 \times 10^{-9}$ | 0.0007 | 8.7 (4-19.2) | Ppdpfb |
| BICF2S23322760 | 12 | 5992526 | A/G | 0.79/0.30 | $8.59 \times 10^{-9}$ | 0.0007 | 8.7 (4-19.2) | Ppdpfb |
| rs8760645 | 12 | 6024841 | T/A | 0.79/0.30 | $8.59 \times 10^{-9}$ | 0.0007 | 8.7 (4-19.2) | Ppdpfb |
| rs9245050 | 12 | 6028685 | G/A | 0.79/0.30 | $8.59 \times 10^{-9}$ | 0.0007 | 8.7 (4-19.2) | Ppdpfb |
| BICF2P863589 | 12 | 6059850 | A/G | 0.88/0.47 | $4.83 \times 10^{-7}$ | 0.0419 | 8 (3.3-19.7) | Ppdpfb |
| BICF2P1115728 | 12 | 6064245 | C/A | 0.88/0.47 | $4.83 \times 10^{-7}$ | 0.0419 | 8 (3.3-19.7) | Ppdpfb |
| BICF2P1254053 | 12 | 6149213 | G/A | 0.84/0.35 | $7.23 \times 10^{-9}$ | 0.0006 | 9.6 (4.2-22.2) | MLN |
| BICF2P402427 | 12 | 6160615 | A/C | 0.79/0.30 | $8.59 \times 10^{-9}$ | 0.0007 | 8.7 (4-19.2) | Ggnbp1 |
| rs8694179 | 12 | 6164202 | A/G | 0.84/0.35 | $7.23 \times 10^{-9}$ | 0.0006 | 9.6 (4.2-22.2) | Ggnbp1 |
| BICF2P459960 | 12 | 6184107 | G/A | 0.84/0.35 | $7.23 \times 10^{-9}$ | 0.0006 | 9.6 (4.2-22.2) | Ggnbp1 |
| BICF2S22951431 | 12 | 6197313 | A/C | 0.79/0.30 | $8.59 \times 10^{-9}$ | 0.0007 | 8.7 (4-19.2) | Ggnbp1 |
| BICF2P1261424 | 12 | 6200280 | G/A | 0.84/0.35 | $7.23 \times 10^{-9}$ | 0.0006 | 9.6 (4.2-22.2) | Ggnbp1 |
| rs9120943 | 12 | 6218850 | A/G | 0.84/0.35 | $7.23 \times 10^{-9}$ | 0.0006 | 9.6 (4.2-22.2) | |
| rs9077055 | 12 | 6238545 | A/G | 0.84/0.35 | $7.23 \times 10^{-9}$ | 0.0006 | 9.6 (4.2-22.2) | |
| rs8677516 | 12 | 6257019 | G/A | 0.86/0.36 | $2.87 \times 10^{-9}$ | 0.0002 | 10.5 (4.4-25) | |
| BICF2P608380 | 12 | 6289014 | G/A | 0.86/0.36 | $2.87 \times 10^{-9}$ | 0.0002 | 10.5 (4.4-25) | |
| rs9132539 | 12 | 6299459 | A/G | 0.79/0.30 | $1.96 \times 10^{-8}$ | 0.0017 | 8.5 (3.9-18.6) | |
| BICF2P1340012 | 12 | 6311277 | C/A | 0.79/0.30 | $8.59 \times 10^{-9}$ | 0.0007 | 8.7 (4-19.2) | |
| BICF2P1211546 | 12 | 6320910 | A/G | 0.79/0.30 | $8.59 \times 10^{-9}$ | 0.0007 | 8.7 (4-19.2) | |
| BICF2P738783 | 12 | 6342204 | A/C | 0.79/0.29 | $6.06 \times 10^{-9}$ | 0.0005 | 9.2 (4.1-20.3) | LOC1127664 |
| BICF2P1313789 | 12 | 6653816 | A/G | 0.79/0.34 | $1.89 \times 10^{-9}$ | 0.0163 | 7.1 (3.3-15.4) | NUDT3 |
| BICF2P1380652 | 12 | 6809061 | A/G | 0.79/0.33 | $8.07 \times 10^{-8}$ | 0.0070 | 7.5 (3.4-16.2) | SPDEF |
| BICF2P1462329 | 12 | 6832252 | A/G | 0.79/0.33 | $8.07 \times 10^{-8}$ | 0.0070 | 7.5 (3.4-16.2) | SPDEF |

In Table 1, Chr stands for chromosome; $P_{OS}$ stands for physical position; $A_R$, stands for risk allele; $A_{NR}$ stands for nonrisk allele; $F_A$ stands for allele frequency in cases; $F_U$ stands for allele frequency in controls; and OR stands for odds ratio.

Permutation testing using 100,000 permutations identified an additional four SNPs that reached genome-wide permuted significance within the DLA II locus and a second region of significance within the STYX gene on chromosome 8 ($P_{raw}$=2.11×10', $P_{permuted}$=0.045) with an odds ratio of 5.9 (95% CI:2.7-12.5) (FIG. 3b and Table 2). FIG. 3b showed that MaxT 100,000 permutation testing was performed and negative log P values were plotted across the genome. The horizontal dotted line represents the threshold for significant association after permutation testing of −log (P)>1.3 with one SNP on chromosome 8 maintaining permuted significance.

FIG. 1 showed all 38 SNPs in the DLA class II region of Chromosome 12 with disease and non-disease associated alleles listed. FIG. 2 showed the sole SNP discovered in the STYX region on Chromosome 8, with disease and non-disease associated alleles listed. To account for the fact that several of the control dogs were younger than the mean age of disease onset at the time of sample acquisition, the data was re-analyzed excluding all control dogs less than 24 months of age. Both the DLA and chromosome 8 regions remained significant with Bonferroni correction and permutation testing, respectively, but the significance was not improved by this exclusion.

Example 3

Identifying Disease-Associated Haplotype Blocks Over the 4.1 MB Region of DLA II on Chromosome 12

Figure 4:
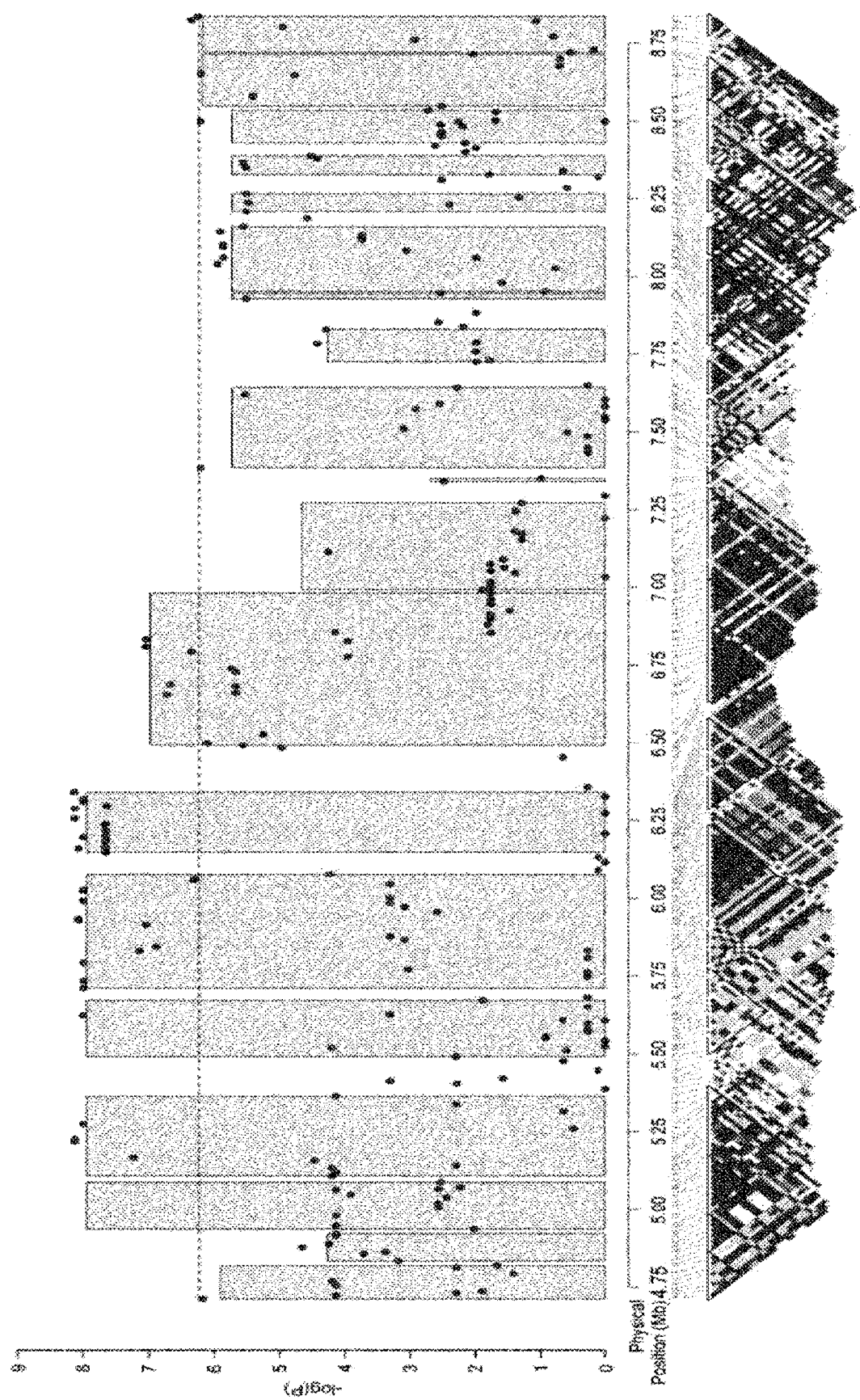
FIG. 4 depicts haplotype analysis of NME-associated DLA II locus on chromosome 12. A 4.1 Mb region located from positions 4,713,392 to 8,834,652 with 19 haplotype blocks generated in Haploview. Negative log P values from single SNP associations were derived from genome-wide analysis after removal of population outliers and individual SNPs were plotted as red circles. The horizontal dotted line represents the threshold for significant association after Bonferroni correction of $-\log(P) > 6.24$.

Haplotype analysis using Haploview (Barrett et al. 2005) identified 19 haplotype blocks across a 4.1 Mb region of DLA II on chromosome 12, all of which were associated with an increased risk for developing NME with P values ranging from $2.1 \times 10^{-3}$ to $1.13 \times 10^{-8}$ (FIG. 4 and Table 3). This 4.1 Mb region located from positions 4,713,392 to 8,834,652 of the genomic DNA sequence on Chromosome 12 (SEQ ID NO:1, available in the canFam2 Canine genomic sequence database) was shown in FIG. 4 with 19 haplotype blocks generated in Haploview (Gabriel et al. 2002). Negative log P values from single SNP associations were derived from genome-wide analysis after removal of population outliers and individual SNPs were plotted as circles. The horizontal dotted line represents the threshold for significant association after Bonferroni correction of −log(P)>6.24. Each haplotype is described by a group of individual tagging SNP genotypes (or alleles) that are associated with risk. The presence of some or all of these alleles

TABLE 2

New SNPs discovered with genome-wide significance after permutation testing

| Canine SNP | Chr | Pos | $A_R/A_{NR}$ | $F_A/F_U$ | $P_{raw}$ | $P_{permuted}$ | OR [95% CI] | Gene |
|---|---|---|---|---|---|---|---|---|
| BICF2S23516667 | 8 | 31971609 | A/G | 0.73/0.32 | $2.11 \times 10^{-6}$ | 0.0452 | 5.9 [2.8-12.5] | STYX |
| BICF2P639740 | 12 | 6686088 | G/A | 0.79/0.33 | $1.30 \times 10^{-7}$ | 0.0283 | 7.5 [3.4-16.4] | NUDT3 |
| BICF2P535495 | 12 | 6793393 | A/G | 0.79/0.33 | $1.30 \times 10^{-7}$ | 0.0453 | 7.5 [3.4-16.4] | MGC8455 |
| rs8957837 | 12 | 8822596 | C/G | 0.77/0.33 | $3.94 \times 10^{-7}$ | 0.0356 | 6.7 [3.1-14.6] | LOC112577 | will determine the risk status. For example, the tagging SNPs in Table 1 that fall in a haplotype block in Table 3 can determine the presence of that block. Based on the tagging SNPs genotype, the risk status of the haplotype block can be determined. When look at the entire 4.1 Mb region, the presence of one or more risk associated haplotype blocks can determine the risk of NME. Further, among these 23 haplotype blocks (Table 3 and Table 4), Block 4 is further described, i.e. the risk status of the haplotype block can be determined, by a combination of tagging SNPs for which the risk alleles are at position 5166878=A, 5217389=G, 5227499=G and 5275229=A. Similarly, Block 5 contains tagging SNPs for which position the risk alleles are at 5622709=C; Block 6 contains tagging SNPs for which the risk alleles are at position 5710832=A, 5734305=A, 5791672=G, 5829667=A, 5843592=G, 5916360=A, 5931001=G, 5935549=A, 5992526=A, 6024841=T, 6028685=G, 6059850=A, 6064245=C; Block 7 contains tagging SNPs for which the risk alleles are at position 6149213=G, 6160615=A, 6164202=A, 6184107=G, 6197313=A, 6200280=G, 6218850=A, 6238545=A, 6257019=G, 6289014=G, 6299459=A, 6311277=C, 6320910=A, and 6342204=A; Block 8 contains tagging SNPs for which the risk alleles are at position 6653816=A, 6686088=G, 6793393=A, 6809061=A and 6832252=A; and Block 19 contains tagging SNPs for which the risk allele is at position 8822596=C (see Table 1 and Table 3).

TABLE 3

19 Haplotype blocks generated by Haploview for DLA II region of Chr. 12

| Block | Haplotype | Population frequency | Case frequency | Control frequency | Start-end position | SEQ ID NO: |
|---|---|---|---|---|---|---|
| 1 | AAGGAGAAA | 0.59 | 0.84 | 0.43 | 4713392-4821633 | 3 |
| 2 | AGGCAAG | 0.60 | 0.80 | 0.47 | 4836721-4923170 | 4 |
| 3 | GCAGGAGGGGA | 0.49 | 0.79 | 0.30 | 4938082-5088561 | 5 |
| 4 | AAAACAGGAAGAG | 0.49 | 0.79 | 0.30 | 5108726-5364188 | 6 |
| 5 | AGAAAGCGA | 0.49 | 0.79 | 0.30 | 5491709-5672682 | 7 |
| 6 | AAGGAGAAAGAGAGAATGGACA | 0.49 | 0.79 | 0.30 | 5710832-6078099 | 8 |
| 7 | GAAGAGAAGGACAGA | 0.49 | 0.79 | 0.30 | 6149213-6342204 | 9 |
| 8 | GGAACAGGAAAAGAGAGGGCGAA | 0.51 | 0.79 | 0.33 | 6492201-6982375 | 10 |
| 9 | CGGGAAAAGGGGAGGC | 0.67 | 0.88 | 0.53 | 6992493-7270218 | 11 |
| 10 | AG | 0.73 | 0.88 | 0.64 | 7338759-7350261 | 12 |
| 11 | AAAAAG | 0.50 | 0.75 | 0.34 | 7384390-7643147 | 13 |
| 12 | AGGAGA | 0.70 | 0.89 | 0.58 | 7725530-7830733 | 14 |

TABLE 3-continued

19 Haplotype blocks generated by Haploview for DLA II region of Chr. 12

| Block | Haplotype | Population frequency | Case frequency | Control frequency | Start-end position | SEQ ID NO: |
|---|---|---|---|---|---|---|
| 13 | AG | 0.50 | 0.75 | 0.34 | 7927872-7944953 | 15 |
| 14 | AATAAAAGAGACGA | 0.50 | 0.75 | 0.34 | 7950821-8158994 | 16 |
| 15 | GGAGG | 0.50 | 0.75 | 0.34 | 8208369-8265940 | 17 |
| 16 | GCAAAG | 0.50 | 0.75 | 0.34 | 8327142-8386063 | 18 |
| 17 | GGCGAGCAAAA | 0.50 | 0.75 | 0.34 | 8429601-8533350 | 19 |
| 18 | ATGAACCG | 0.51 | 0.77 | 0.34 | 8546686-8713747 | 20 |
| 19 | GGCA | 0.51 | 0.77 | 0.34 | 8719506-8834652 | 21 |

Manually forcing all of these haplotype blocks into a single haplotype resulted in the creation of a 4.1 Mb haplotype containing 241 SNPs (SEQ ID NO: 1). This haplotype was common and strongly associated with an increased risk of developing NME at a case frequency of 85.1%, control frequency at 38.4% with significance p value at $7.97 \times 10^{-7}$. The strong association of the NME disease with DLA II supports an autoimmune etiology. Haplotype analysis of the DLA II region identified a large, common block strongly associated with altered disease risk. Polygenic loci with MHC II polymorphisms show the strongest disease association, as observed between DLA II and NME association.

Example 4

Identifying Disease-Associated Haplotype Blocks Over the 488 kb Region of STYX on Chromosome 8

Figure 5:
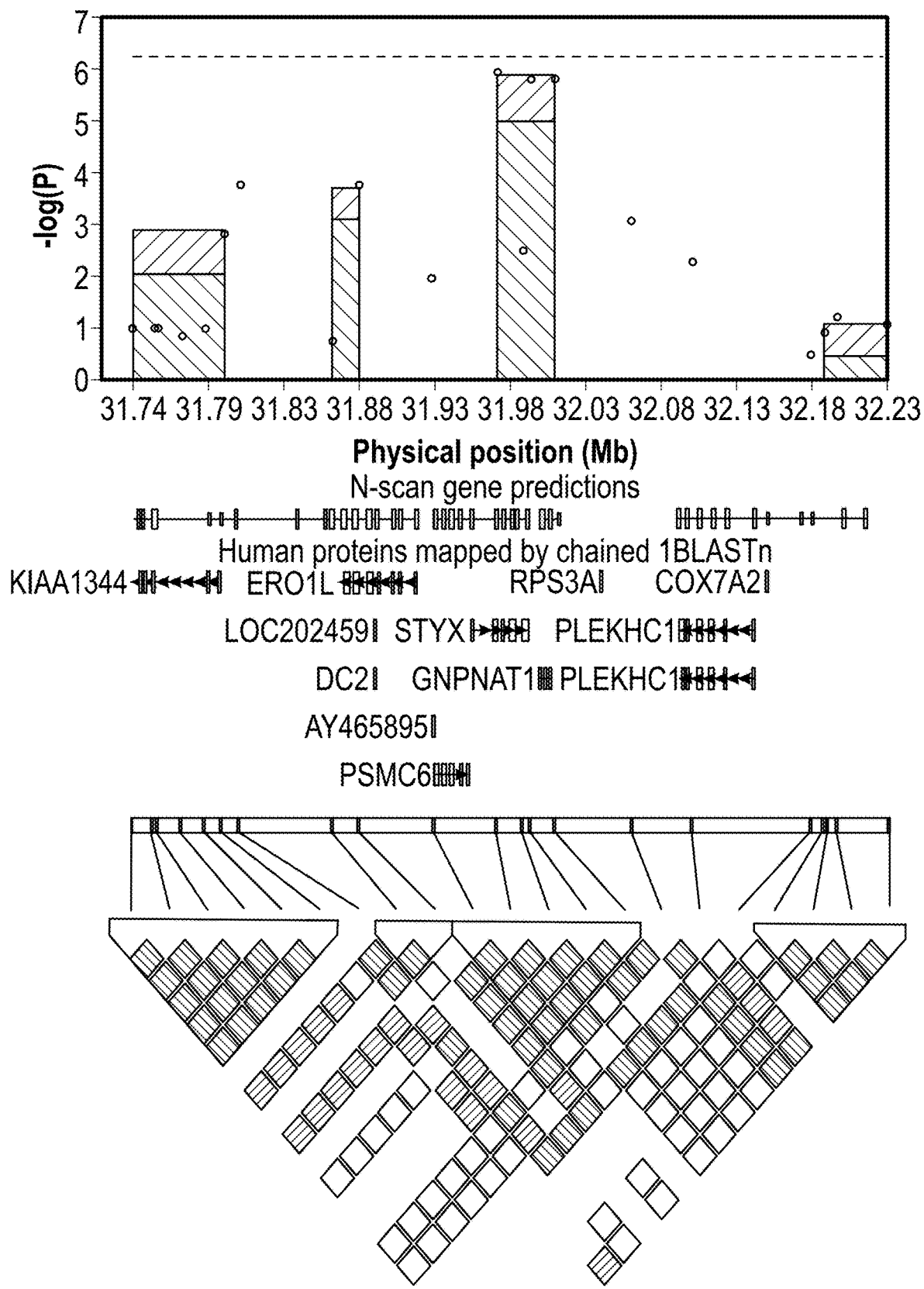
FIG. 5 depicts haplotype analysis of NME-associated locus on chromosome 8. A 488 kb region located from positions 31,736,206 to 32,225,068 is shown with 4 haplotype blocks generated in Haploview. Negative log P values from single SNP associations were derived from genome-wide analysis after removal of population outliers and individual SNPs were plotted as red circles. The horizontal dotted line represents the threshold for significant association after Bonferroni correction of $-\log(P) > 6.24$. The additional blue region within each haplotype block represents MaxT 100,000 permuted haplotypes.

Haplotype analysis of the STYX region of chromosome 8 identified four haplotypes (FIG. 5 and Table 4). A 488 kb region located from positions 31,736,206 to 32,225,068 of the genomic DNA sequence (SEQ ID NO: 2, available in the canFam2 Canine genomic sequence database) is shown in FIG. 5 with 4 haplotype blocks generated in Haploview. Negative log P values from single SNP associations were derived from genome-wide analysis after removal of population outliers and individual SNPs were plotted as circles. The horizontal dotted line represents the threshold for significant association after Bonferroni correction of −log(P)>6.24. The additional shaded region within each haplotype block represents MaxT 100,000 permuted haplotypes.

TABLE 4

Haplotype blocks generated by Haploview for STYX region of Chr.8

| Block | Haplotype | Population frequency | Case frequency | Control frequency | Start position | End Position | SEQ ID NO: |
|---|---|---|---|---|---|---|---|
| 20 | GAAGGG | 0.74 | 0.59 | 0.83 | 31736206 | 31795128 | 22 |
| 21 | AG | 0.47 | 0.27 | 0.59 | 31866373 | 31883390 | 23 |
| 22 | GGAG | 0.52 | 0.27 | 0.68 | 31971609 | 32009283 | 24 |
| 23 | AGAA | 0.50 | 0.59 | 0.44 | 32183184 | 32225068 | 25 |

The most significantly associated and common haplotype spanned the STYX and GNPNAT1 genes and was protective based on phenotype (P=1.43×10$^{-6}$). This block also contained two additional haplotypes significantly associated with NME risk (p~0.005, data not shown).

STYX, (serine/threonine/tyrosine interacting protein) is a pseudophosphatase that lacks intrinsic catalytic activity and is structurally similar to members of the dual-specificity phosphatase subfamily of protein tyrosine phosphatases. Protein tyrosine phosphatases play a key role in immune system function including lymphocyte activation, with mutations in PTPN22 having been documented in association with autoimmunity (Vang et al. 2005). STYX also is known to bind to the calcineurin substrate CRHSP-24, and calcineurin plays an important role in T cell activation. Dephosphorylation of CRHSP-24 can be prevented by administration of the immunomodulatory drugs cyclosporine and FK506.

GNPNAT1, glucosamine-phosphate N-acetyltransferase 1, is involved in amino sugar metabolism including the formation of uridine diphospho-N-acetylglucosamine (UDP-GlcNAc). UDP-GlcNAc is an important cellular metabolite necessary for the synthesis of of N-linked and O-linked glycans that play important roles in normal thymic T-cell apoptosis. The disruption of GNPNAT1 is expected to lead to aberrant immune responses in NME.

The purpose of this investigation was to identify disease susceptibility loci for NME through genome-wide association (GWA) of single nucleotide polymorphisms (SNPs) in affected and non-affected Pug dogs. 170,000 SNPs, genome-wide association was performed on a small number of case and control dogs to determine disease susceptibility loci in canine necrotizing meningoencephalitis (NME), a disorder with known non-Mendelian inheritance that shares clinical similarities with atypical variants of multiple sclerosis in humans. Genotyping of 30 NME-affected Pug dogs and 68 healthy, control Pugs identified two loci associated with NME, including a region within dog leukocyte antigen class II on chromosome 12 that remained significant after Bonferroni correction. Our results support the utility of this high density SNP array, confirm that dogs are a powerful model for mapping complex genetic disorders and provide important preliminary data to support in depth genetic analysis of NME in numerous affected breeds.

Example 5

Identifying Disease-Associated Indels Over the 4.1 MB Region of DLA II on Chromosome 12

Next-generation whole genome sequencing utilizing the Illumina chemistry (Illumina, San Diego, Calif.) was performed to identify a functional variant within the 4.1 Mb associated haplotype on chromosome 12. Three neuropathologically verified affected pugs and two closely matched unaffected pugs over the age of 6 years were used for the sequencing. The genomes of the five dogs were sequenced to an average coverage of 13.5× and, averagely, 5 million SNPs and small indel variants per animal were identified. Among these SNPs and indels, a single base deletion causing a frame shift in the major histocompatibility complex, class II, DP beta 1 (HLA-DPB1; human leukocyte antigen-DPB1) gene was discovered. This particular HLA-DPB1 single base deletion is located at 333 KB downstream from the most strongly associated SNP previously identified, BICF2P194998. The HLA-DPB1 deletion variant is represented by SEQ ID NO: 26 (5'-TCTTCGCGCAATTG-GACAGCGCGGCGGGGGTGTTCGCGGCCG TGTCGAGCTGGGCCGAGTAACTGCCAGGAACT GGAACGTCCCCGG-3'), and a "C" is deleted at Chromosome 12 position 5608903, in comparison to the HLA-DPB1 wild type (UniProKB/Swiss-Prot No: P04440) represented by SEQ ID NO: 27 (5'-TCTTCGCGCAATTGGACA-GCGCGGCGGGGGTGTTCGCGGCCG TGTCCGAGCTGGGCCGAGTAACTGCCAGGAACTG GAACGTCCCCGG-3'). This HLA-DPB1 deletion variant is in haplotype Block 5.

Example 6

HLA-DPB1 Deletion Variant Confirmation

The Sanger sequencing was performed on 93 pugs (26 post-mortem confirmed NME cases and 67 unaffected controls) to test if the HLA-DPB1 deletion variant was more strongly associated with NME than the previously genotyped SNPs. The P-values and odds ratios were calculated by Fisher's exact allelic tests to demonstrate the strength of NME association. Fisher's exact allelic tests showed that the HLA-DPB1 deletion was more strongly associated with NME with 1.285e-15, OR 23.2 (86.5% frequency in all cases and 21.6% in controls). The deletion variant in HLA-DPB1 is therefore the leading candidate for the functional variant within the DLA locus associated with genetic risk for NME in the pug. The deletion variant was found in 22 out of 60 investigated control dogs over 6 years of age and was found in all case dogs that were histopathologically confirmed, and such finding further indicated the non-Mendelian inheritance pattern of NME in those animals.

HLA-DPB1 belongs to the HLA class II beta chain paralogues. This class II molecule is a heterodimer consisting of an alpha (DPA) and a beta chain (DPB), both anchored in the membrane. Class II molecules are expressed in antigen presenting cells (APC) such as, B lymphocytes, dendritic cells, macrophages. HLA-DPB1 binds peptides derived from antigens that access the endocytic route of APC and presents them on the cell surface for recognition by the CD4 T-cells. HLA-DPB1 variants have been linked to multiple human disorders with autoimmune associations including lupus, multiple sclerosis, and Graves' disease. This particular HLA-DPB1 single base deletion located at 333 KB downstream from NME associated SNP BICF2P194998 enables development of further diagnostic tests, treatment approaches within the pug, and a further investigation of haplotype positive animals as possible models for human autoimmune diseases.

Example 7

Materials and Methods

Diagnosis:

Affected dogs included 8 Malteses with histopathologically confirmed NME disease and 3 with a diagnosis based on clinical presentation, magnetic resonance imaging, and cerebrospinal fluid analysis. Control Maltese dogs had no evidence of neurological or autoimmune disease at the time of sample collection.

In addition to Maltese, 16 case (i.e., afflicted with NME) and 9 control Chihuahua and 34 case and 88 control Pug, were studied for meta-analysis. The Pug dogs are an expansion of the dataset used by R M Barber et al., Identification of risk loci for necrotizing meningoencephalitis in Pug dogs, J. Hered. (102) Suppl:S40-6 (2010). The Chihuahua cases were histopathologically confirmed and the controls had no evidence of neurological or autoimmune disease at the time of sample collection.

Genotyping:

DNA samples were either extracted from blood, saliva or formalin-fixed tissue sections embedded in paraffin. Genomic DNA was extracted from the EDTA blood samples using the DNeasy extraction kit (Qiagen, Venlo, Netherlands). Saliva samples were extracted using the Oragene Saliva extraction protocol (DNA Genotek, Kanata, Canada) and the FFPE tissues were extracted using the QIAamp DNA FFPE Tissue Kit (Qiagen, Venlo, Netherlands), followed by Ovation whole genome amplification (Ovation WGA FFPE system; NuGEN, San Carlos, USA). Samples were genotyped using the CanineHD beadchip, following manufacturer's instructions (Illumina Inc, San Diego, USA).

Figure 6:
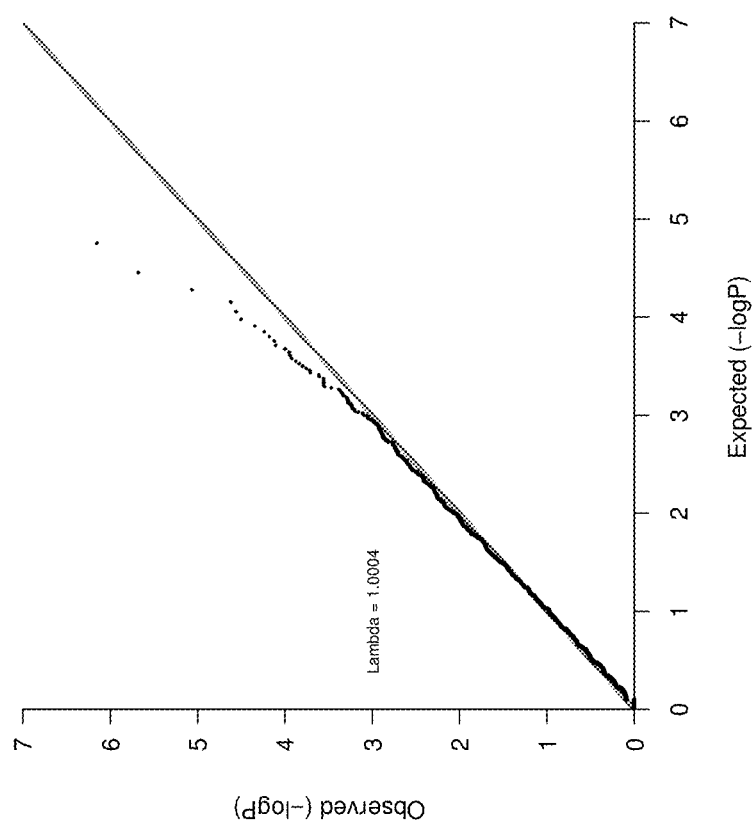
FIG. 6 is a QQ plot of the Maltese population used in the experiments detailed herein.

Statistical Analysis:

A total of 173662 SNPs were genotyped on 11 NME cases and 38 controls. Genome-wide analysis was performed with plink v1.07 (S. Purcell *PLINK: a tool set for whole genome association and population-based linkage analyses*, Am. J. Hum. Genet. (81) 559-75 (2007)). Pairwise IBD estimation was done to remove possibly related dogs (Pi_hat score >0.5 were excluded), leading to the exclusion of 1 control (Pi_hat score: 0.64). Next, multidimensional scaling (MDS) with a minor allele frequency (MAF) of <0.10 and genotype frequency >97% was performed to determine population stratification, and 2 controls that were not clustered with the main population of dogs were excluded resulting in a final population of 11 NME cases and 35 controls for analysis. Further testing of population stratification was done on this sample set by plotting a QQplot of observed against expected p-values, resulting in a genomic inflation factor of 1.025, or 1.0004 when corrected for the two associated regions (FIG. 6), demonstrating no significant population stratification in the sample set. The Pug and Chihuahua populations after quality control and MDS consisted of 32 case 44 control Pugs and 16 case and 9 control Chihuahua.

All samples had a call rate of >80% and were included in the analysis. After excluding SNPs <97% and MAF >0.10, HWE >0.001, and SNPs on the X and Y chromosomes, a total of 57222 SNPs were analyzed. A bonferroni correction for multiple testing was performed with a resulting P value of $8.7 \times 10^{-7}$ across 57222 SNPs for genome-wide significance. To further evaluate genome-wide significance MaxT permutation testing of 10 000 permutations was applied and a FDR correction was applied (Benjamini & Hochberg (1995) step-up FDR control). All plots were created using R2.15.3 (packages qqman and ggplot2).

Meta-Analysis:

To calculate the common effect size of the SNPs across the different populations, meta-analysis and corresponding forest plots were done using the R package Rmeta and R2.15.3 on the Maltese, Chihuahua and Pug populations. The common OR was estimated by a logistic regression model with origin and genotype as independent variables, and outcome as dependent variable (the Mantel-Haenszel method). In addition, genome wide meta-analysis was performed using plink v1.07. Power calculations were done using the genetic power calculator, assuming 29% carrier frequency, a relative risk of 5.45 in the homozygotes, a disease frequency of 1% and considering unscreened random controls (K A Greer et al., Necrotizing meningoencephalitis of Pug dogs associates with dog leukocyte antigen class II and resembles acute variant forms of multiple sclerosis, Tissue Antigens (76) 110-118 (2010)).

Association Testing

Association testing in the Maltese revealed two regions that reach genome wide significance: Chr4: 74522353T>A $p=8.07 \times 10-7$, and chr15: 53338796A>G $p=1.55 \times 10-7$ (Table 5 and FIG. 11). All genes in these regions were then prioritized based on ENDEAVOUR gene prioritization with a training set of human MS genes (L-C Tranchevent et al., ENDEAVOUR update: a web resource for gene prioritization in multiple species, Nucleic Acids Res. (36) W377-384 (2008).

Figure 12A:
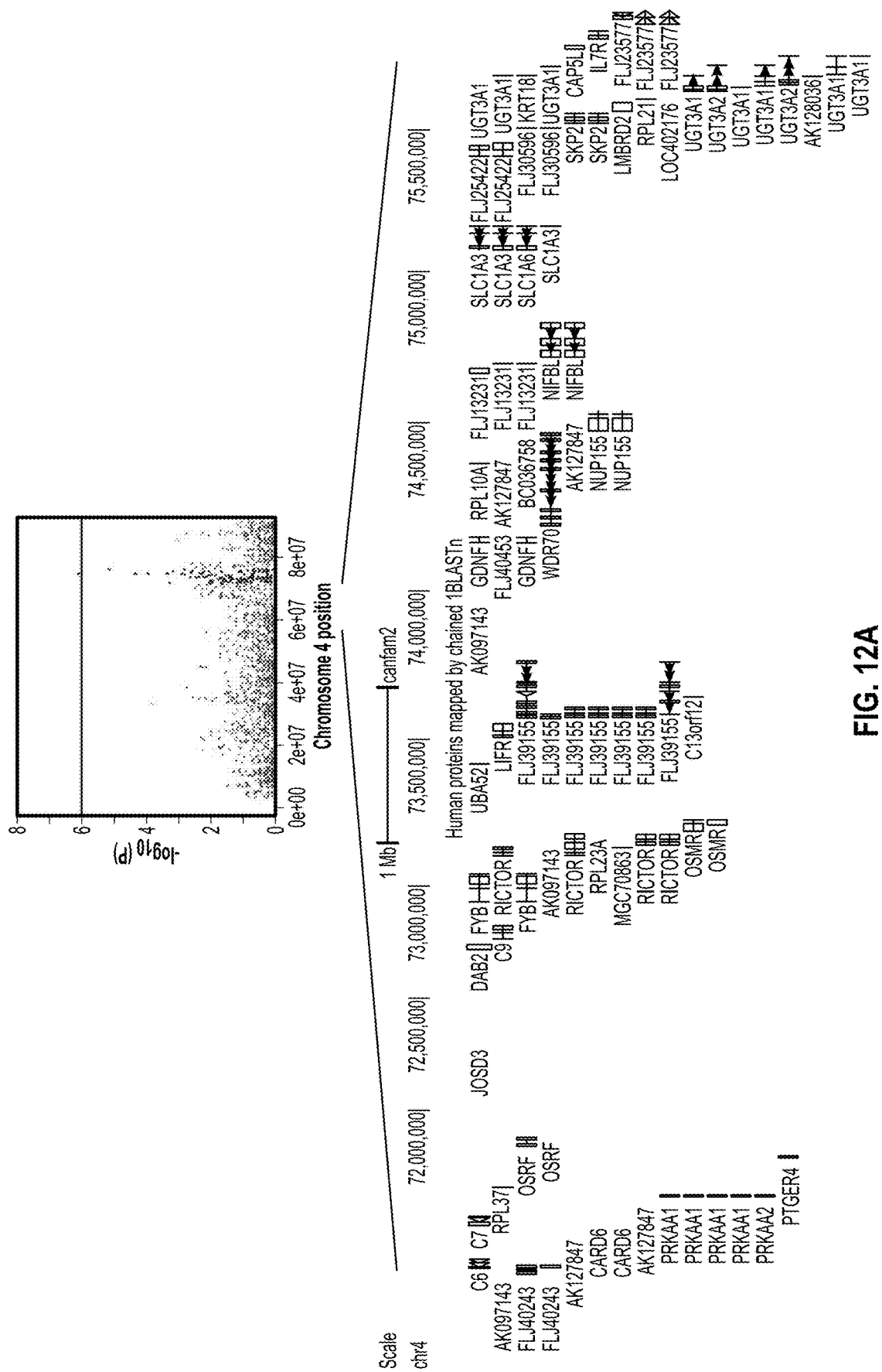
FIGS. 12A and 12B are a series of regional Manhattan plots for the regions on chr4 and chr15, respectively, and the genes located in these regions. The associated region is highlighted in blue. The horizontal grey line represents the threshold for significant association after Bonferroni correction.
Figure 12B:
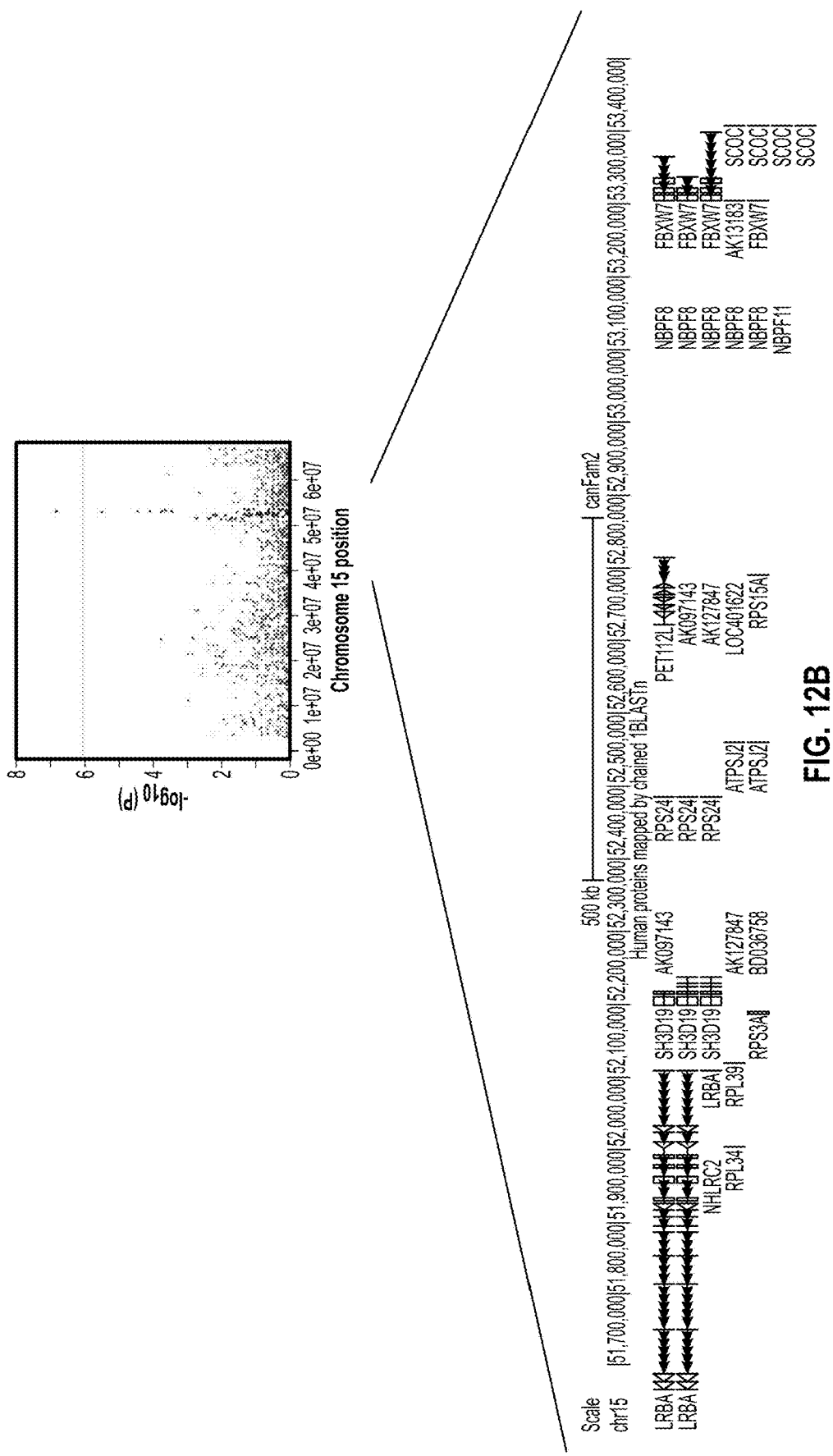

The following genes were prioritized in each region: IL7R (encodes for the IL7 receptor alpha chain) and FBXW7α, which can be found on chromosomes 4 and 15, respectively (Table 6 and FIGS. 12A and 12B). None of the SNPs in the Chihuahua population reached genome wide significance, due to low sample size. 139 SNPs and 237 in the IL7R region were also genotyped in the Chihuahua and Pug respectively, but only 5 reached nominal significance in each (p<0.05). 55 and 75 SNPs were genotyped in the region on chr15 in the Chihuahua and Pug respectively, and 3 (5.5%) and 18 (24%) reached nominal significance respectively. In the Pug, this is much higher than expected (5%).

TABLE 5

| Chr | Position | SNP | $P_{raw}$ | BONF | FDR_BH | Max(T) | AF cases | AF control | OR | L95 | U95 |
|---|---|---|---|---|---|---|---|---|---|---|---|
| 4 | 74332455 | BICF2G630168115 | 4.52E−05 | 1.000 | 0.157 | 0.696 | 0.82 | 0.31 | 9.818 | 2.972 | 32.440 |
| 4 | 74457236 | BICF2G630168169 | 4.52E−05 | 1.000 | 0.157 | 0.696 | 0.82 | 0.31 | 9.818 | 2.972 | 32.440 |
| 4 | 74522353 | BICF2G630168244 | 8.07E−07 | 0.039 | 0.013 | 0.027 | 0.91 | 0.31 | 21.820 | 4.684 | 101.600 |
| 4 | 75929427 | BICF2P1021800 | 7.16E−06 | 0.348 | 0.058 | 0.199 | 0.00 | 0.49 | 0 | | |
| 15 | 53260054 | BICF2P1314960 | 3.52E−05 | 1.000 | 0.156 | 0.593 | 0.45 | 0.04 | 18.270 | 4.269 | 78.200 |
| 15 | 53272289 | BICF2P956368 | 3.19E−06 | 0.155 | 0.031 | 0.097 | 0.50 | 0.04 | 22.330 | 5.361 | 93.040 |
| 15 | 53338976 | rs8954494 | 1.55E−07 | 0.008 | 0.008 | 0.005 | 0.60 | 0.04 | 33.500 | 7.763 | 144.600 |

Table 5: Top 3 SNPs from each of the associated regions; Praw: Fisher exact test p-value. BONF: Bonferroni correction for multiple testing. FDR: False discovery rate of multiple testing; Max(T): Max(T) permutation of 10000 permutations, EMP2 value; AF: Allele frequency; L95: OR:

Odds ration; 95% CI lower boundary; U95: 95% CI. Coordinates are based on CanFam2.0 alignment.

TABLE 6

Table 2: Human proteins mapped to the 2 identified regions in the canine genome (tBlastN).

| chr4 | chr15 |
|---|---|
| AK097143 | AK097143 |
| AK127847 | AK127847 |
| AK128036 | AK131383 |
| BC036758 | ATP5J2 |
| C13orf12 | BC036758 |
| C6 | FBXW7 |
| C7 | LOC401622 |
| C9 | LRBA |
| CAPSL | NBPF11 |
| CARD6 | NBPF8 |
| DAB2 | NHRC2 |
| FLJ13231 | PET112L |
| FLJ23577 | RPL34 |
| FLJ25422 | RPL39 |
| FLJ30596 | RPS15A |
| FLJ39155 | RPS24 |
| FLJ40243 | RPS3A |
| FLJ40453 | SCOC |
| FYB | SH3D19 |
| GDNF | |
| IL7R | |
| JOSD3 | |
| KRT18 | |
| LIFR | |
| LMBRD2 | |
| LOC402176 | |
| MGC70863 | |
| NIPBL | |
| NUP155 | |
| OSMR | |
| OSRF | |
| PRKAA1 | |
| PTGER4 | |
| RICTOR | |
| RPL10A | |
| RPL21 | |
| RPL23A | |
| RPL37 | |
| SKP2 | |
| SLC1A3 | |
| UBA52 | |
| UGT3A1 | |
| UGT3A2 | |
| WDR70 | |

Table 6: Human proteins mapped to the 2 identified regions in the canine genome (tBlastN).

Next, the dog leukocyte antigen (DLA) II locus on chr12:4,713,392-8,834,652 in the Maltese (FIG. 8) and the Chihuahua (FIG. 9) were analyzed. Of the 122 SNPs genotyped in this area in the Maltese, 17 (13.9%) were significant (p<0.05), which is higher than expected (5%). The most significant SNP is: BICF2P178662 chr12:5166878 (p=0.001) (FIG. 10). In the Chihuahua, 120 SNPs were genotyped that passed quality control, of which 8 are significant (6.6%). The most significant SNP is: BICF2P608380 chr12: 6289014 (p=0.006) (FIG. 10). 13 SNPs and 9 SNPs were analyzed in the region associated with NME in the Pug dog on chr8 (chr8:31736206-32225068) in the Maltese and Chihuahua respectively, but none of SNPs reached significance.

Meta-Analysis of the DLA II Region in the Pug, Maltese and Chihuahua

To look more closely to the DLAII region, a meta-analysis was performed on the SNPs in the DLAII locus and the Maltese population, a Chihuahua population and an expanded Pug population of the population described previously R M Barber et al., Identification of risk loci for necrotizing meningoencephalitis in Pug dogs, J. Hered. (102) Suppl:S40-6 (2010). FIG. 10 shows the SNPs that were most significant in the Pug (BICF2P738783, BICF2P22942), Maltese (BICF2P178662) and Chihuahua (BICF2P608380) that were genotyped and passed QC in all 3 cohorts. The effect sizes are similar between all populations. Power calculations show that the Maltese and Chihuahua data-sets have respectively 52% and 38% power to detect the previous effect present in the Pug when using an allelic test (K A Greer et al., Necrotizing meningoencephalitis of Pug dogs associates with dog leukocyte antigen class II and resembles acute variant forms of multiple sclerosis, Tissue Antigens (76) 110-118 (2010); and S Purcell et al., Genetic Power Calculator: design of linkage and association genetic mapping studies of complex traits, Bioinformatics (19) 149-150 (2003)). In addition, a meta-analysis was also performed on SNPs from the chr7 and chr15 region, which also demonstrated a similar effect size in all breeds for the region on chr15 (FIG. 11). Meta-analysis across the entire genome designated the HLAII regions as genome wide significant ($p=1.18\times10-8$), followed by the region on chr15 ($p=2.23\times10-6$).

Figure 7:
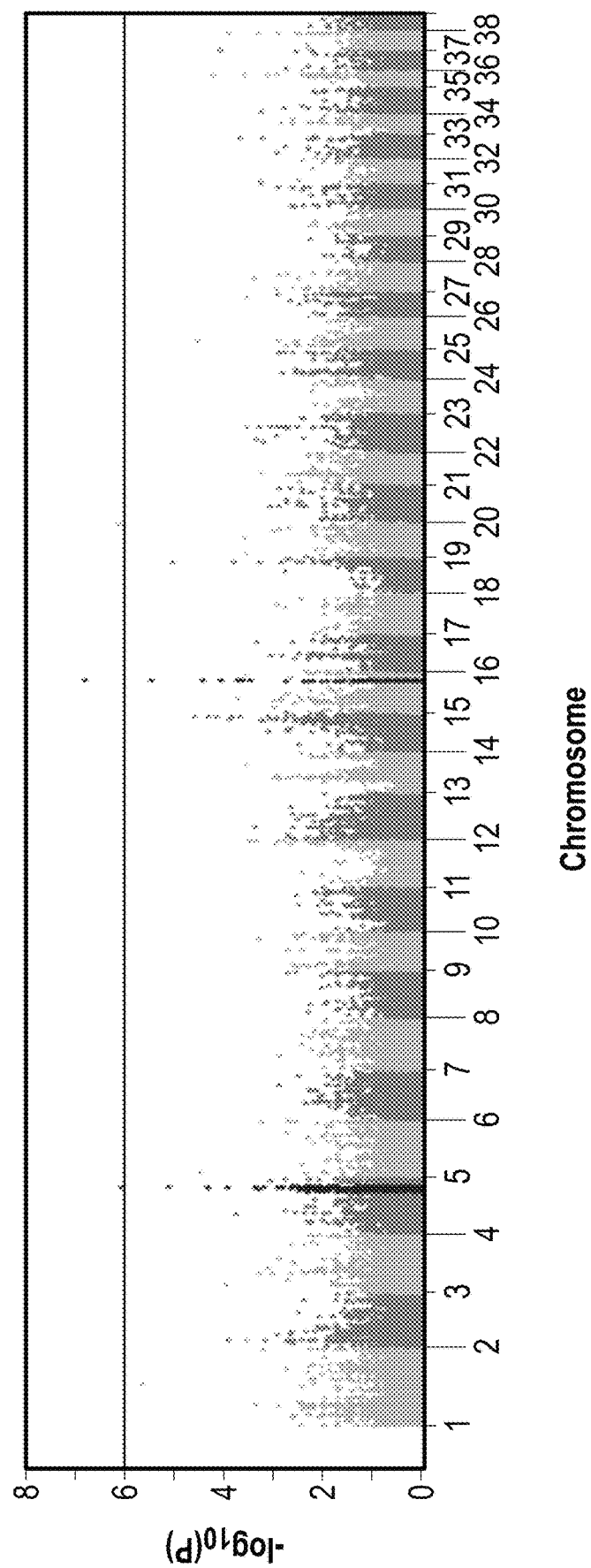
FIG. 7 is a Manhattan plot of the Maltese population in which regions that reach genome wide significance are indicated in black. The horizontal grey line represents the threshold for significant association after Bonferroni correction.

Overall, a genome wide association study in the Maltese dog was performed to identify susceptibility loci for NME. As described above, the study 2 risk loci associated with disease (FIG. 7), on chr4 and chr15.

The region on chr4 spreads about 10 Mb, with the highest significance between chr4: 71506894-75929427 (4.4 Mb). About 44 human proteins map to this region in the canine genome (tBlastN) (Table 6). The most significant gene of interest/marker in this region is IL7R (encodes for the IL7 receptor alpha chain), which is located about 68,000 bp from significant marker BICF2P1021800 (Table 5). Polymorphisms in IL7R, have been demonstrated to contribute to the non-HLA genetic risk in multiple sclerosis in humans. In addition, an altered expression of the genes encoding IL7Ralpha and its ligand, IL7, has been found in the cerebrospinal fluid compartment of individuals with multiple sclerosis (F. Lundmark et al., Variation in interleukin 7 receptor alpha chain (IL7R) influences risk of multiple sclerosis, Nature Genetics (39) 1108-1113 (2007)). IL7R is a member of the type I cytokine receptor family, an important immune system regulator and important in the proliferation and survival of T and B lymphocytes.

The second region on chr15 spreads about 1.9 Mb at chr15:51567064-53471253 and 19 human proteins map to this region (Table 6). An interesting gene in this region is FBXW7, which is an important attenuator of inflammatory signaling. FBW7α regulates CCAAT enhancer binding protein-delta (C/EBPδ), by its requirement for ubiquitination and degradation of C/EBPδ. C/EBPδ binding to its own promoter increases when FBW7α is silenced. C/EBPδ is a transcription factor that regulates inflammatory processes mediating bystander neuronal injury and CNS autoimmune inflammatory disease. Data from experiments performed in mice lacking C/EBPδ suggest that C/EBPδ may have a role in systemic inflammatory diseases such as multiple sclerosis. Mice deficient in C/EBPδ expression exhibited less severe clinical disease than wild-type littermates in response to induction of experimental autoimmune encephalomyelitis (EAE) by vaccination with a myelin oligodendrocyte glycoprotein (MOG) fragment.

Another interesting gene is LRBA. Deleterious mutations in LRBA have been associated with a syndrome of immune deficiency and autoimmunity. By performing meta-analysis, similar effect sizes were found for this region in the Pug, Chihuahua and Maltese, and an enrichment of nominal associated SNPs in the Pug. This suggests this region might also be important in other Toy breeds (FIG. 11).

Figure 8:
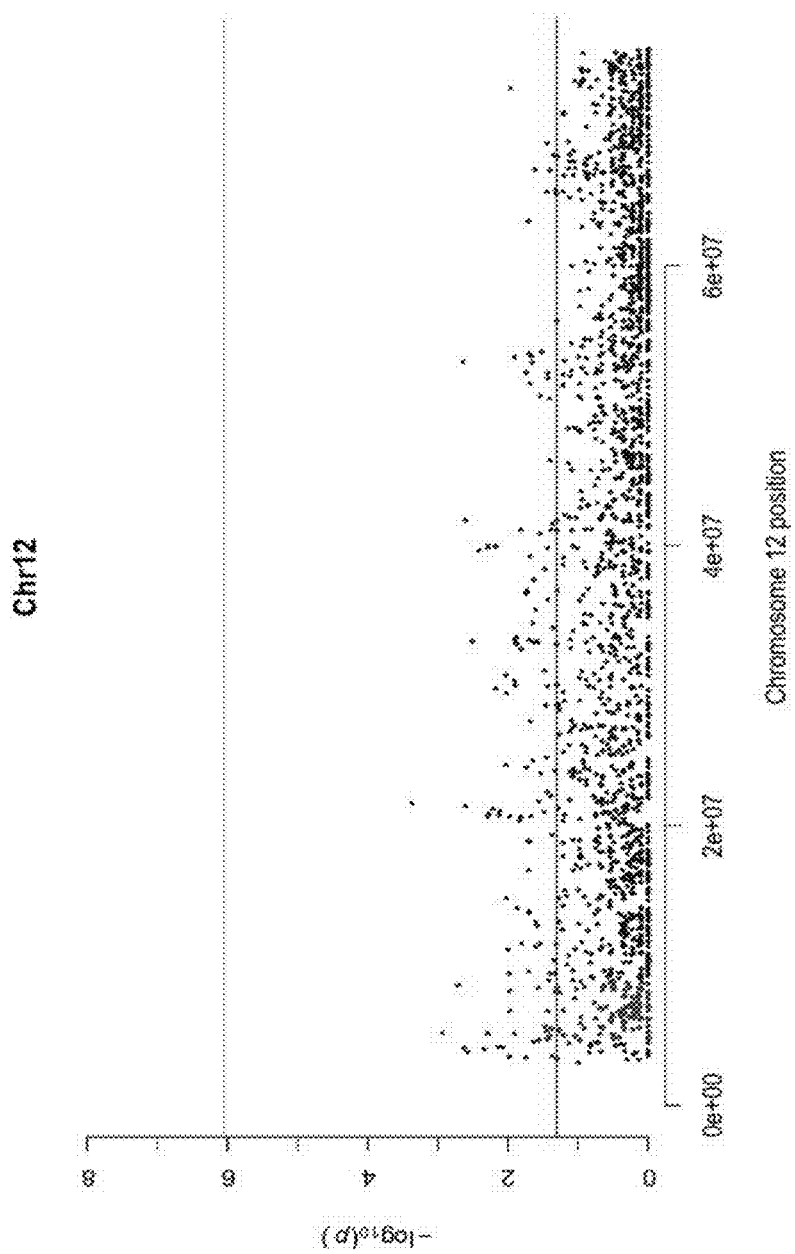
FIG. 8 is a regional Manhattan plot for the DLA II region on chromosome 12 (chr12) in the Maltese. The associated region is labeled Region 100. The horizontal grey line labeled 102 represents the threshold for significant association after Bonferroni correction. The line labeled 104 represents a $p=0.05$ cut-off.
Figure 9:
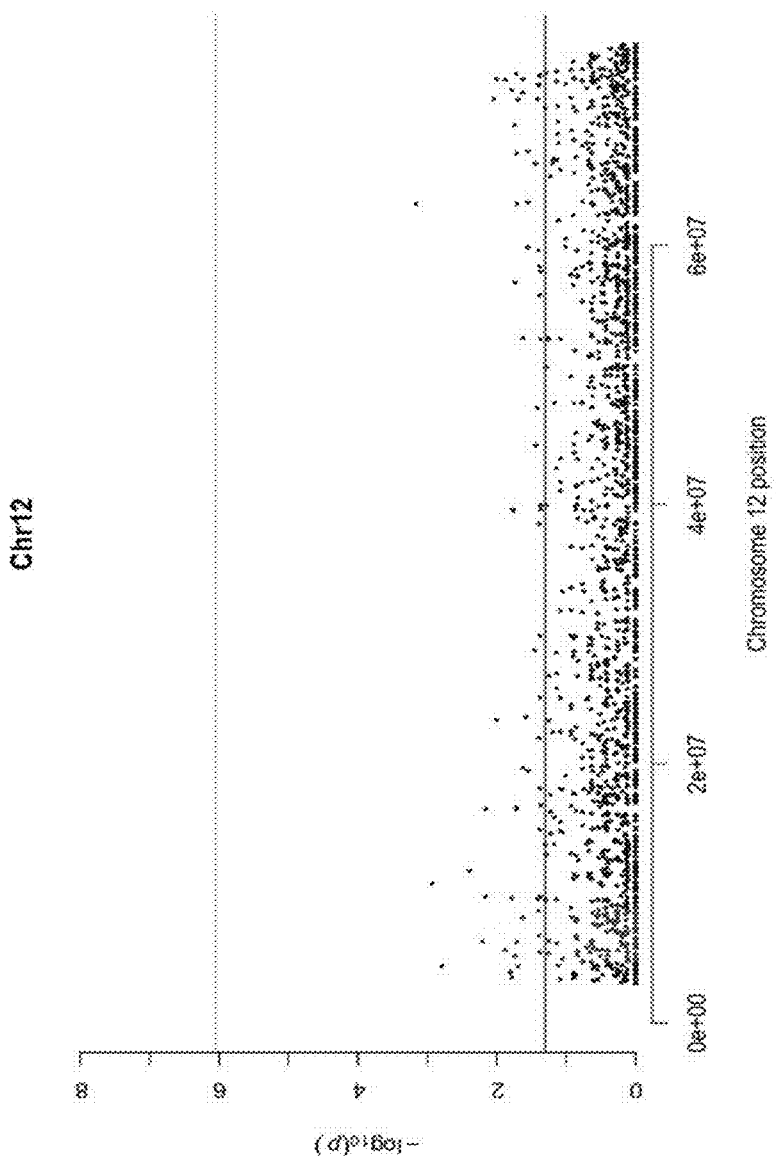
FIG. 9 is a regional Manhattan plot for the DLA II region chr12 in the Chihuahua. The associated region is labeled Region 200. The horizontal line labeled 202 represents the threshold for significant association after Bonferroni correction. The line labeled 204 represents a $p=0.05$ cut-off.
Figure 10:
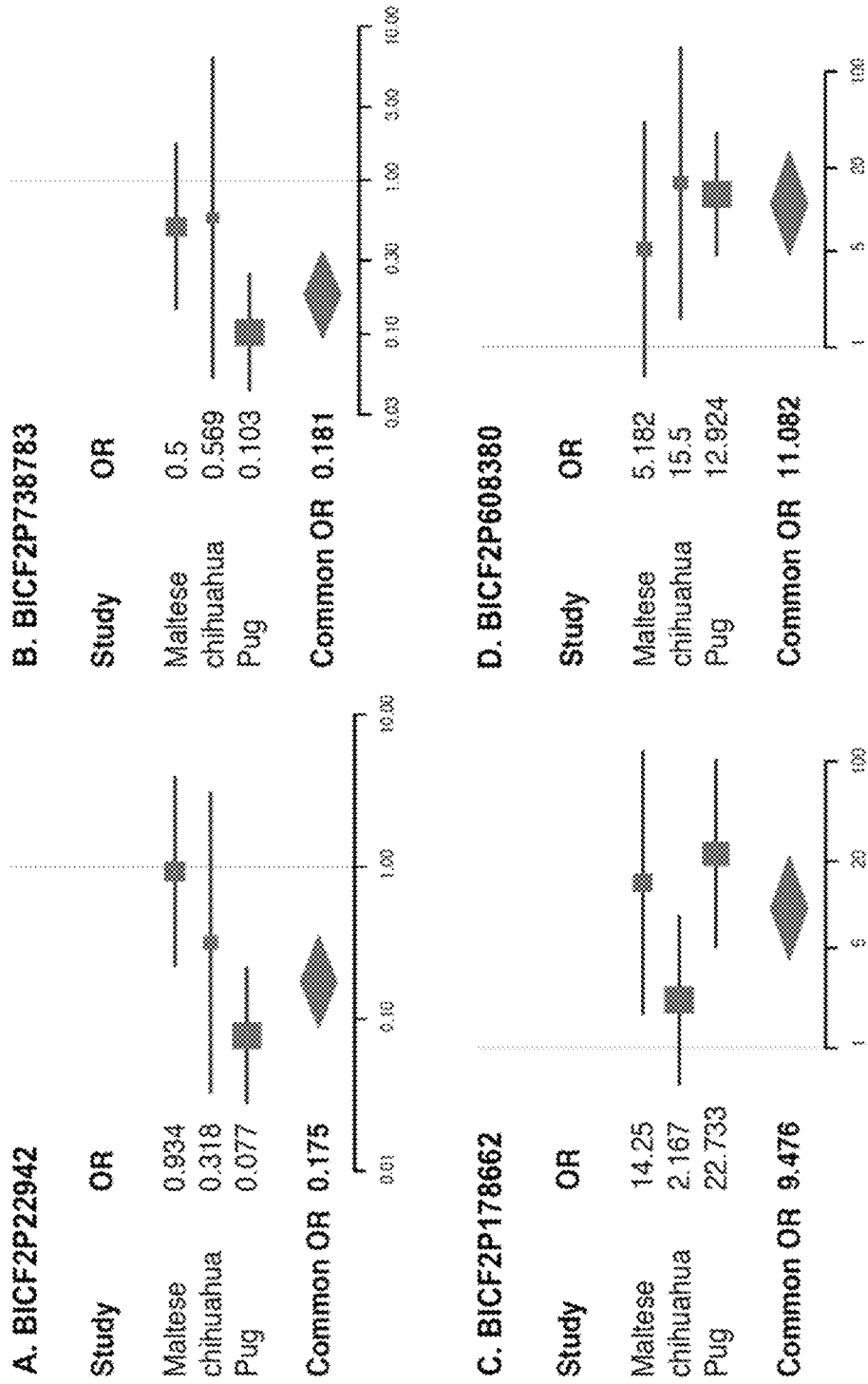
FIG. 10 is a series of Forest plots for 4 SNPs in the DLAII region across the 4 toy breeds. The 95% confidence interval for each study is given by a horizontal line, and the point estimate is given by a square, the height of which is inversely proportional to the standard error of the estimate after each study. The summary odds ratio is indicated by a diamond with horizontal limits at the confidence limits and width inversely proportional to its standard error. The meta-analyses for all these SNPs are significant and effect sizes are in the same direction. BICF2P178662: $p=1.11 \times 10^{-9}$ (OR=9.48 [4.19-21.40]); BICF2P738783: $p=4.11 \times 10^{-8}$ (OR=0.18 [0.10-0.34]); BICF2P22942: $p=1.57 \times 10^{-7}$ (OR=0.18 [0.09-0.35]); BICF2P608380: $p=8.6 \times 10^{-11}$ (OR=11.08 [4.72-26.01])
Figure 11:
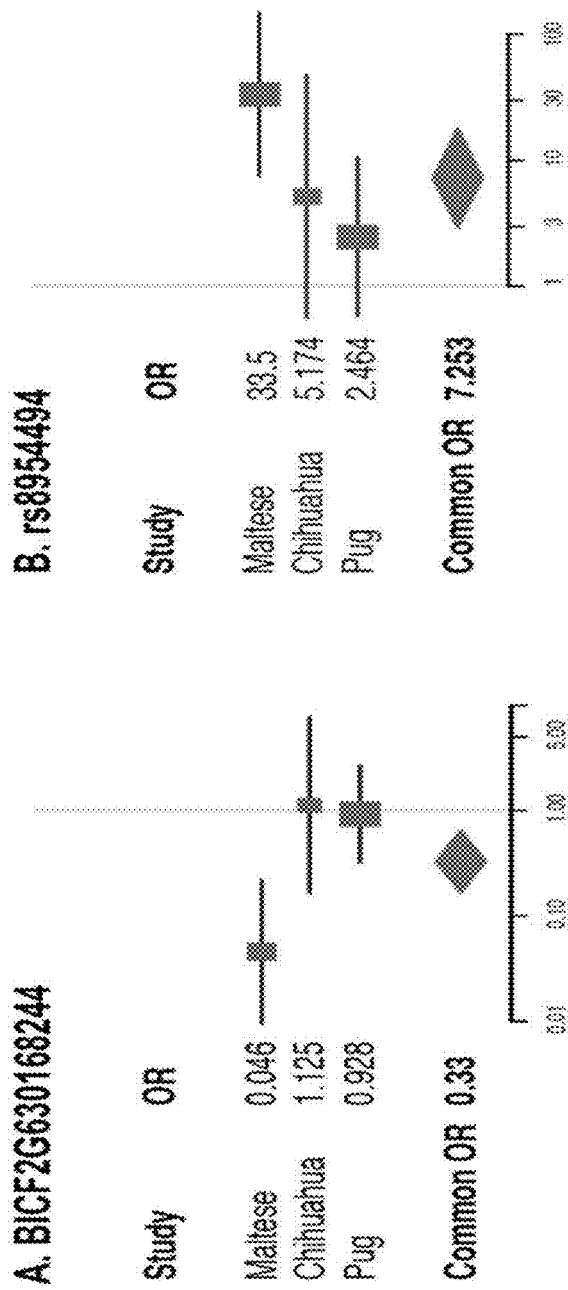
FIG. 11 is series of Forest plots for the most significant SNPs in the Maltese (CFA4 and CFA15) across the 3 toy breeds. The 95% confidence interval for each study is given by a horizontal line, and the point estimate is given by a square, the height of which is inversely proportional to the standard error of the estimate after each study. The summary odds ratio is indicated by a diamond with horizontal limits at the confidence limits and width inversely proportional to its standard error. The meta-analyses for all these SNPs are significant and effect sizes are in the same direction. TIGRP2P203665_rs8954494: $p=2.54 \times 10'$ (OR=7.25 [2.94-17.91]); BICF2G630168244: $p=6.59 \times 10^{-4}$ (OR=0.33 [0.17-0.65])

Association of the DLA II locus (chr12) with NME in the Maltese and Chihuahua was analyzed, since DLA II (or MHC II) is strongly associated with NME in the Pug and multiple sclerosis in humans (FIGS. 8-10). There is an enrichment of SNPs reaching nominal significance and similar effect sizes between breeds (FIG. 10), though effect sizes might be lessened in the Maltese and Chihuahua. A genome-wide meta-analysis indicates this region as a region reaching genome wide significance across all breeds (FIG. 10). This suggests that DLA II is a shared risk factor for NME across several canine breeds and different species with a similar disease pathogenesis (multiple sclerosis in humans).

In the foregoing description, the technology has been described with reference to specific exemplary embodiments. Various modifications and changes may be made, however, without departing from the scope of the present technology as set forth. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10770183B2). An electronic copy of the "Sequence Listing" will also be available from the USPTO upon request and payment of the fee set forth in 37 CFR 1.19(b)(3).

We claim:

1. A method for treating a canine subject for necrotizing meningoencephalitis (NME), the method comprising:
   extracting genomic DNA from a sample from the canine subject;
   assaying the genomic DNA for one or more single nucleotide polymorphisms (SNPs), wherein the SNPs comprise BICF2G630168244 corresponding to position 74522353 on canine chromosome 4 and rs8954494 corresponding to position 53338796 on canine chromosome 15;
   detecting an A allele at BICF2G630168244 and a G allele at rs8954494 in the genomic DNA from the sample; and
   administering an effective amount of an immunosuppressive treatment to the canine subject having the A allele at BICF2G630168244 and a G allele at rs8954494 in the genomic DNA from the sample.

2. The method according to claim 1, wherein the canine subject is selected from the group consisting of Pug, Chihuahua, and Maltese.

3. The method according to claim 1, further comprising assaying the genomic DNA for one or more SNPs selected from the group consisting of: BICF2P608380 corresponding to position 1575622 on SEQ ID NO: 1 and BICF2P178662 corresponding to position 453486 on SEQ ID NO: 1.

4. The method according to claim 1, further comprising assaying the genomic DNA for one or more SNPs selected from the group consisting of: BICF2S23225431 corresponding to position 503997 on SEQ ID NO: 1, BICF2P22942 corresponding to position 514107 on SEQ ID NO: 1, BICF2P194998 corresponding to position 561837 on SEQ ID NO: 1, rs8856588 corresponding to position 909317 on SEQ ID NO: 1, BICF2P574765 corresponding to position 997440 on SEQ ID NO: 1, BICF2P1186632 corresponding to position 1020913 on SEQ ID NO: 1, BICF2P1185629 corresponding to position 1078280 on SEQ ID NO: 1, BICF2P540937 corresponding to position 1116275 on SEQ ID NO: 1, rs9189886 corresponding to position 1130200 on SEQ ID NO: 1, rs9006653 corresponding to position 1202968 on SEQ ID NO: 1, BICF2P1200278 corresponding to position 1217609 on SEQ ID NO: 1, rs9125534 corresponding to position 1222157 on SEQ ID NO: 1, BICF2S23322760 corresponding to position 1279134 on SEQ ID NO: 1, rs8760645 corresponding to position 1311449 on SEQ ID NO: 1 rs9245050 corresponding to position 1315293 on SEQ ID NO: 1, BICF2P863589 corresponding to position 1346458 on SEQ ID NO: 1, BICF2P1115728 corresponding to position 1350853 on SEQ ID NO: 1, BICF2P1254053 corresponding to position 1435821 on SEQ ID NO: 1, BICF2P402427 corresponding to position 447223 on SEQ ID NO: 1, rs8694179 corresponding to position 1450810 on SEQ ID NO: 1, BICF2P459960 corresponding to position 1470715 on SEQ ID NO: 1, BICF2S22951431 corresponding to position 1483921 on SEQ ID NO: 1, BICF2P1261424 corresponding to position 1486888 on SEQ ID NO: 1, rs9120943 corresponding to position 1505458 on SEQ ID NO: 1, rs9077055 corresponding to position 1525153 on SEQ ID NO: 1, rs8677516 corresponding to position 1543627 on SEQ ID NO: 1, rs9132539 corresponding to position 1586067 on SEQ ID NO: 1, BICF2P1340012 corresponding to position 1597885 on SEQ ID NO: 1, BICF2P1211546 corresponding to position 1607518 on SEQ ID NO: 1, BICF2P738783 corresponding to position 1628812 on SEQ ID NO: 1, BICF2P1313789 corresponding to position 1940424 on SEQ ID NO: 1, BICF2P639740 corresponding to position 1972696 on SEQ ID NO: 1, BICF2P535495 corresponding to position 2080001 on SEQ ID NO: 1, BICF2P1380652 corresponding to position 2095669 on SEQ ID NO: 1, BICF2P1462329 corresponding to position 2118860 on SEQ ID NO: 1, rs8957837 corresponding to position 4109204 on SEQ ID NO: 1, BICF2S23516667 corresponding to position 235408 on SEQ ID NO: 2, BICF2P608380 corresponding to position 1575622 on SEQ ID NO: 1 and BICF2P178662 corresponding to position 453486 on SEQ ID NO: 1.

5. The method according to claim 1, wherein the assaying the genomic DNA comprises a method selected from the group consisting of Sanger sequencing, next generation sequencing, pyrosequencing, sequencing by ligation, sequencing by synthesis, single molecule sequencing, pooled and barcoded DNA sequencing, PCR, real-time PCR, quantitative PCR, microarray analysis of genomic DNA, restriction fragment length polymorphism analysis, allele specific ligation, and comparative genome hybridization.

6. A method for breeding a canine subject to reduce propensity to necrotizing meningoencephalitis (NME) in progeny resulting from the breeding, the method comprising:
    extracting genomic DNA from a sample from the canine subject;
    assaying the genomic DNA for one or more single nucleotide polymorphisms (SNPs), wherein the SNPs comprise BICF2G630168244 corresponding to position 74522353 on canine chromosome 4 and rs8954494 corresponding to position 53338796 on canine chromosome 15;
    detecting a T allele at BICF2G630168244 and an A allele at rs8954494 in the genomic DNA from the sample; and
    breeding the canine subject with the T allele at BICF2G630168244 and the A allele at rs8954494 in the genomic DNA from the sample.

7. The method according to claim 6, wherein the canine subject is selected from the group consisting of Pug, Chihuahua, and Maltese.

8. The method according to claim 6, wherein the assaying the genomic DNA comprises a method selected from the group consisting of Sanger sequencing, next generation sequencing, pyrosequencing, sequencing by ligation, sequencing by synthesis, single molecule sequencing, pooled and barcoded DNA sequencing, PCR, real-time PCR, quantitative PCR, microarray analysis of genomic DNA, restriction fragment length polymorphism analysis, allele specific ligation, and comparative genome hybridization.

* * * * *